US010568903B2

(12) United States Patent
Broomhead et al.

(10) Patent No.: US 10,568,903 B2
(45) Date of Patent: Feb. 25, 2020

(54) CLAY PRODUCT AND USES THEREOF

(71) Applicant: Oil-Dri Corporation of America, Chicago, IL (US)

(72) Inventors: Jonathan Broomhead, Chicago, IL (US); Fang Chi, Chicago, IL (US); Ron L. Cravens, Chicago, IL (US); George Robert Goss, Chicago, IL (US); Richard Jaffee, Chicago, IL (US); Sara LeAnn Johnston, Chicago, IL (US); Michael McPherson, Chicago, IL (US); Ronda Jean Williams, Chicago, IL (US)

(73) Assignee: Oil-Dri Corporation of America, Chicago ( * ) Notice: Subject to any disclaimer, the term of this patent is extended or adjusted under 35 U.S.C. 154(b) by 8 days.

(21) Appl. No.: 14/044,546

(22) Filed: Oct. 2, 2013

(65) Prior Publication Data

US 2014/0099373 A1 Apr. 10, 2014

Related U.S. Application Data

(60) Provisional application No. 61/792,382, filed on Mar. 15, 2013, provisional application No. 61/708,763, filed on Oct. 2, 2012.

(51) Int. Cl.

| | |
|---|---|
| ***A61K 33/06*** | (2006.01) |
| ***A61K 35/66*** | (2015.01) |
| ***A61K 33/12*** | (2006.01) |
| ***A61K 35/02*** | (2015.01) |
| ***A61K 36/06*** | (2006.01) |
| ***A61K 31/198*** | (2006.01) |

(52) U.S. Cl.
CPC .............. *A61K 33/06* (2013.01); *A61K 33/12* (2013.01); *A61K 35/66* (2013.01)

(58) Field of Classification Search
None
See application file for complete search history.

(56) References Cited

U.S. PATENT DOCUMENTS

| | | | | |
|---|---|---|---|---|
| 4,942,042 | A | 7/1990 | Bhargava | |
| 6,045,834 | A * | 4/2000 | Howes | A23K 10/10 426/2 |
| 7,939,066 | B2 | 5/2011 | Puntenney et al. | |
| 2006/0239992 | A1 | 10/2006 | Puntenney et al. | |
| 2007/0048432 | A1* | 3/2007 | Holzgraefe | A23K 20/163 426/658 |
| 2007/0298013 | A1* | 12/2007 | Altman | A61K 35/74 424/93.3 |
| 2008/0020095 | A1 | 1/2008 | Block et al. | |
| 2010/0178300 | A1 | 7/2010 | Yiannikouris et al. | |
| 2010/0189871 | A1 | 7/2010 | Yu et al. | |
| 2010/0272769 | A1* | 10/2010 | Darlington, Jr. | A01N 59/00 424/409 |
| 2011/0033576 | A1* | 2/2011 | Yiannikouris et al. | 426/60 |

FOREIGN PATENT DOCUMENTS

| | | |
|---|---|---|
| CN | 101878865 B | 9/2012 |
| EP | 1 767 201 | 3/2007 |
| EP | 2314172 A1 | 4/2011 |
| GB | 2 175 205 | 11/1986 |
| JP | S61-260021 | 11/1986 |
| JP | 2006-101784 | 4/2006 |
| JP | 2007-217435 | 8/2007 |
| JP | 2012-515001 | 7/2012 |
| WO | 2006/001492 | 1/2006 |
| WO | 2010/083336 | 7/2010 |
| WO | 2016/019343 | 2/2016 |

OTHER PUBLICATIONS

Lee et al. (Comparative Immunology, Microbiology, & infections Diseases 2007, 30, 261-268).*
Girgis et al. (Veterinary Immunology and Immunopathology 2010, 138, 218-223).*
Ellakany et al. (Trop Anim Health Prod 2011, 43, 249-257).*
Amlan International (Calibrin-Z Product Information from Amlan website dated Oct. 19, 2009).*
Definition: mixture (Oxford English Dictionary accessed Jan. 19, 2016).*
Hofshagen et al. Avian Dis. Oct.-Dec. 1992;36(4):837-43.*
Weese et al. (AAEP Proccedings, vol. 48, 2002, p. 127-130).*
Vondruskova, H et al. Alternatives to Antibiotic Growth Promoters in Prevention of Diarrhoea in Weaned Piglets: A Review. Veterinami Medicina, May 2010, vol. 55, No. 5, pp. 199-224.
Frericks, J. Brewers' Yeast as a Supplement in Aquaculture. iaf_features: The Mobile Friendly Version of International Aquafeed Magazine. May 16, 2012 [online] [retrieved on Dec. 31, 2013] http://iaffeatures.wordpress.com/2012/05/16/brewers-yeast-as-a-supplement-in-aquaculture/.
Agri Trading Investment, Calibrin-Z. Company Profiles and Products, Apr. 16, 2011 [online] [retrieved on Dec. 31, 2013]; http://agritrading-investment.com/?p= 16.
Jaynes, WF et al. Aflatoxin Toxicity Reduction in Feed by Enhanced Binding to Surface-Modified Clay Additives. Toxins, Jun. 10, 2011, Vo. 3, No. 6, pp. 551-565.
International Preliminary Report on Patentability and Written Opinion of the International Searching Authority dated Apr. 7, 2015, which issued during prosecution of International Application No. PCT/US2013/063102.

(Continued)

*Primary Examiner* — Abigail Vanhorn
(74) *Attorney, Agent, or Firm* — Vedder Price, P.C.; Michael J. Turgeon

(57) ABSTRACT

The present invention relates to a combination of an anti-toxin, The present invention relates to a combination of an anti-toxin, an immunomodulator and a component that provides energy to mucosal cells, which may be useful for decreasing effects of *Clostridia* sp. or coccidia sp based diseases or other enteric diseases or by generally improving gastro intestinal health or function.

66 Claims, 18 Drawing Sheets

(56) References Cited

OTHER PUBLICATIONS

European Search Report dated Apr. 22, 2016, which issued during prosecution of European Application No. 13843869.2.
Anonymous: "CitriStim" Apr. 21, 2012, retrieved from: https://web.archive.org/web/20120421153919/http://www.admani.com/CitriStim/CitriStim%20Index.htm.
Anonymous: "CitriStim" Apr. 25, 2012, retrieved from: http://www.lab-inter.com/document/9381.
Anonymous: "Calibrin-Z Agri Trading Investment" Apr. 18, 2011, retrieved from: http://web.archive.org/web/20120130035143/http://agritrading-investment.com/?p=16.
Notice of Reasons for Rejection dated Aug. 14, 2017, which issued during prosecution of Japanese Application No. 2015-535763.
Corthier, et al. "Effect of Oral *Saccharomyces boulardii* Treatment on the Activity of Clostridium Difficile Toxins in Mouse Digestive Tract" Toxicon, 1992, 30(12):1583-1589.
Jiang, et al. "Effect on hepatonephric organs, serum metabolites and oxidative stress in post-weaning piglets fed purified zearalenone-contaminated diets with or without Calibrin-Z" Journal of Animal Physiology and Animal Nutrition, 2012, 96:11-47-1156.
Chinese Second Office Action dated Feb. 24, 2017, which issued during prosecution of Chinese Application No. 201380063040.4.
Russian Office Action dated Sep. 28, 2017, which issued during prosecution of Russian Application No. 2015116892.
Song et al., "Dietary clays alleviate diarrhea of weaned pigs" J. Anim. Sci., Jan. 2012; 90(1):345-60.
Bobrovnichiy, et al. "Disbakteriozy kishechnika u detey: prichiny, diagnostika, lechenie (Enteric Dysbacteriosis in Children: Causes, Diagnostics, Treatment)" Uchebnometodicheskoe posobie, Minsk, 2007.
Grigoryev. "Spravochnoe rukovodstvo po gastroenterologii (Reference Guide on Gastroenterology)", Moscow-MIA, 2003, p. 294-395.
Shpigel. "Dokazatelnaya meditsina (Evidence-Based Medicine)", Arnebiya, 2004, pp. 40-43, 47-49.
Yuryev K.L. et al. "Dokazatelnaya meditsina. Kokranovskoe sotrudnichestvo (Evidence-Based Medicine. Cochrane Collaboration)" Ukrainskiy medichniy chasopis, 2000, XI/XII, No. 6(2):6-15.

* cited by examiner

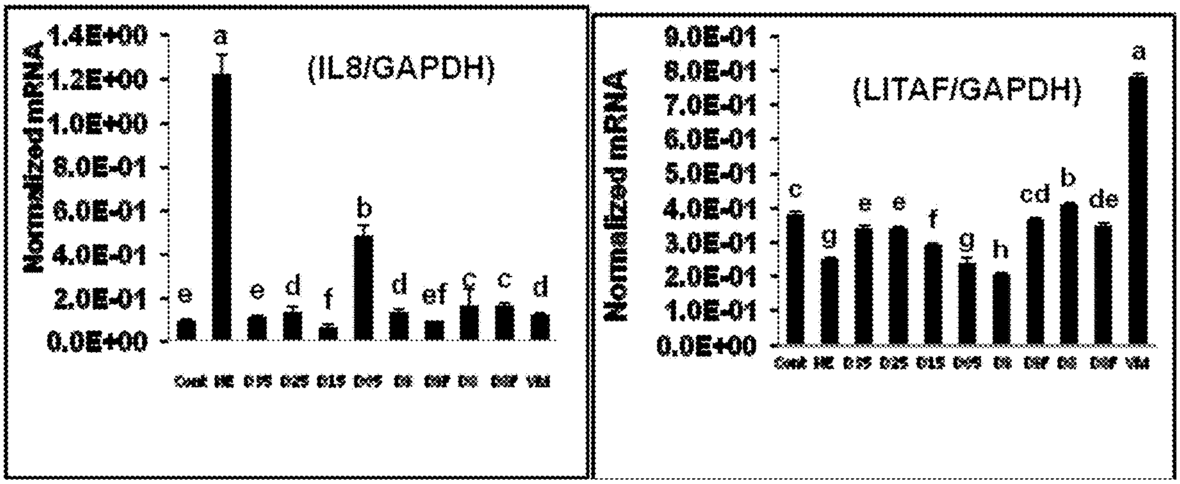
FIGS. 18A-B
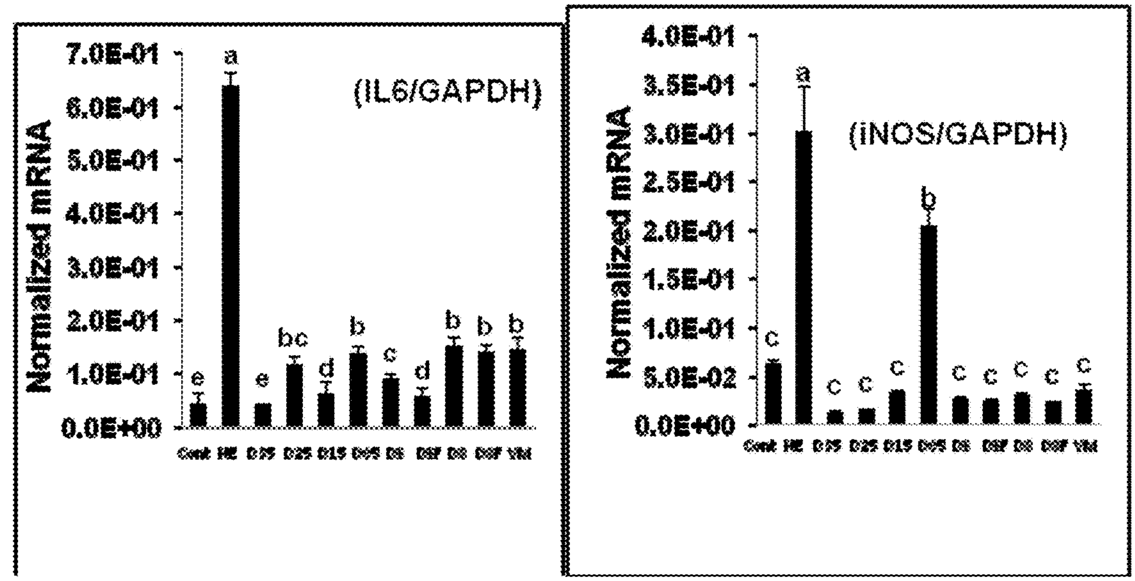
FIGS. 18C-D

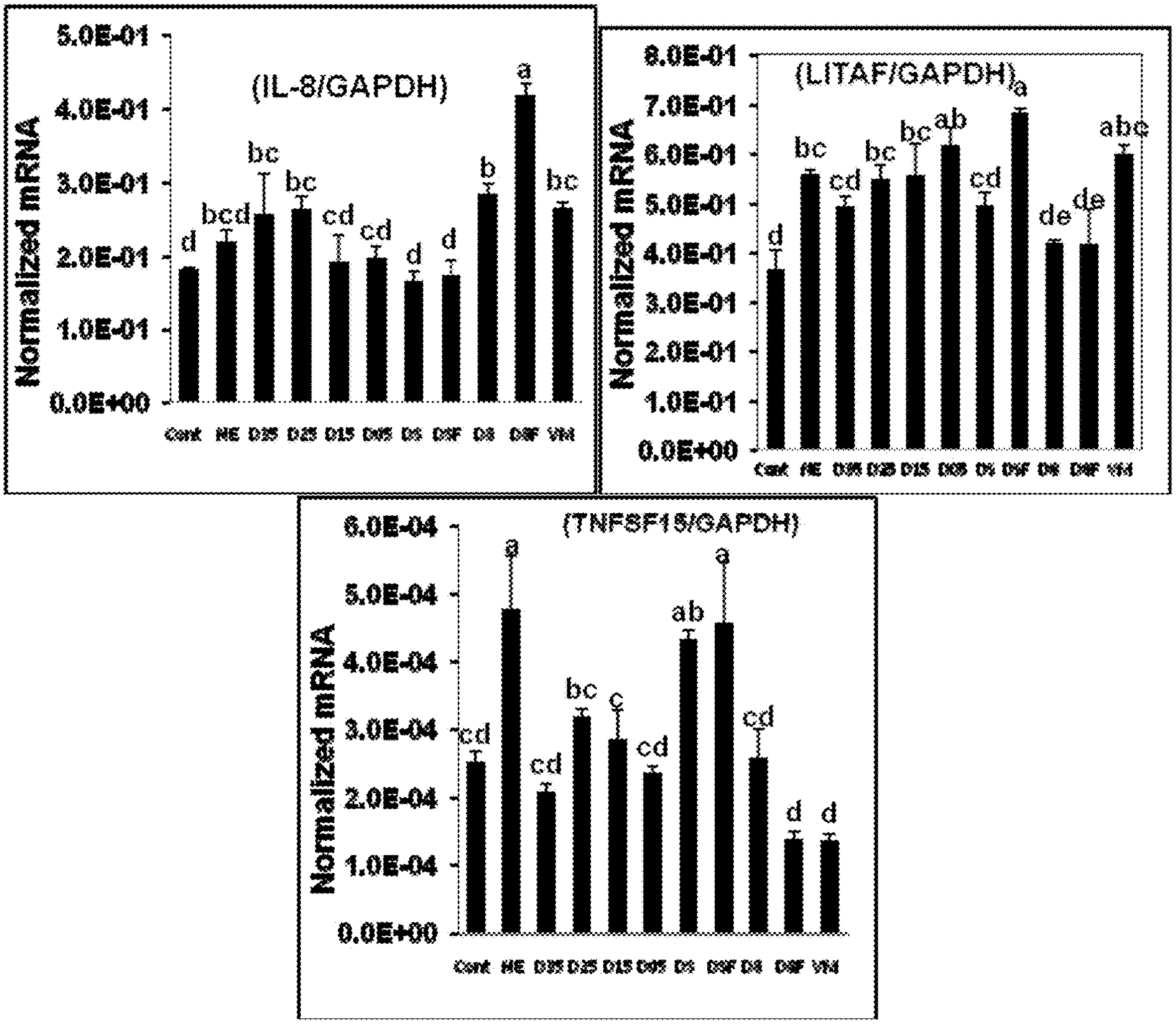
FIGs. 19A-C

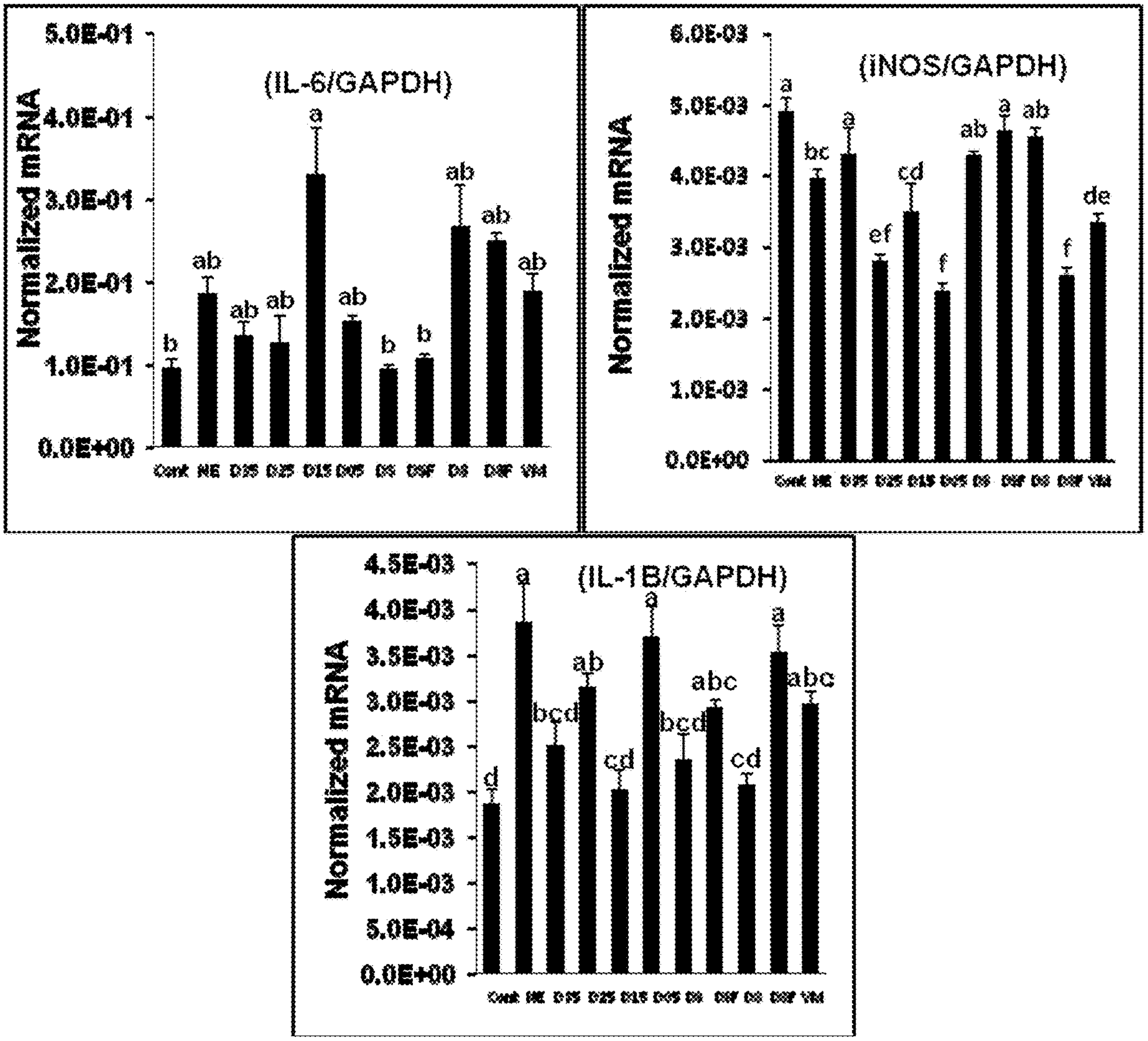
FIG. 19D-F

CLAY PRODUCT AND USES THEREOF

RELATED APPLICATIONS AND INCORPORATION BY REFERENCE

This application claims benefit of and priority to U.S. provisional patent application Ser. Nos. 61/708,763 and 61/792,382 filed Oct. 2, 2012 and Mar. 15, 2013, respectively and entitled "CLAY-CONTAINING COMPOSITION THAT ALLEVIATES EFFECTS OF BACTERIAL EXOTOXIN-ASSOCIATED DISEASE" and "CLAY, A YEAST PRODUCT AND GLUTAMATE BLENDED PRODUCT AND USES THEREOF", respectively.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The application relates to a mixture of clay, a yeast product and optionally, glutamate, and uses thereof, in particular for decreasing effects of an enteric disease.

BACKGROUND OF THE INVENTION

*Clostridium* is a bacterial genus that secrets toxins causing disease in poultry, animals, and humans. Anaerobic bacterial pathogens are a serious economic burden on the agricultural industry. Bacteria of the *Clostridium* family represent a particular burden, because these bacteria cause serious diseases in poultry and other economically valuable domestic animals. Previous efforts to control these organisms have relied upon sanitary measures and the administration of antibiotics in the animal feed.

Necrotic enteritis (NE) is the most common and financially devastating bacterial disease in modern broiler flocks. It is an infectious disease caused by *Clostridium perfringens*, which is a gram-positive, anaerobic bacterium that can be found in soil, litter, dust and at low levels in the intestine of healthy birds. *Clostridium perfringens* only causes NE when it transforms from non-toxin producing type to toxin producing type.

There are five types of *C. perfringens* (A, B, C, D and E) which produce a number of toxins (alpha, beta, epsilon, iota and CPE). The α-toxin, an enzyme (phospholipase C) is believed to be a key to the occurrence of NE. However, a recent study has shown that an isolate that does not produce α-toxin can still cause disease. In addition, a new toxin called NetB has been recently identified in disease causing *C. perfringens* isolates. The intestine of infected birds is friable and distended with gas and gross lesions caused by toxins. In the acute form of NE, birds often die before showing clinical signs. However, in its subclinical form the disease is much more financially damaging for the producer. The commonly observed symptoms of the disease vary with the age of birds.

There remains a need in the art for a safe, economical and effective method of protecting intensively cultivated domestic animals, including avians, such as chickens, from infection by *Clostridium* species. *Clostridia* caused diseases cause both human suffering and economic loss in livestock. A cost-effective manner to intervene in these diseases would aid in disease management systems.

Citation or identification of any document in this application is not an admission that such document is available as prior art to the present invention.

SUMMARY OF THE INVENTION

The present invention relates to an anti-toxin, an immunomodulator, a component that provides energy to mucosal cells, or a combination thereof, which may be useful for decreasing effects of *Clostridia* or coccidia based diseases or other enteric diseases or by generally improving gastro intestinal health or function.

Applicants have shown in vitro that certain clays can adsorb toxins from *Clostridium difficile* and *Clostridium perfringens*. Applicants have shown in vivo that certain clays or clay formulations can alleviate necrotic enteritis in chickens, a disease associated with *Clostridium perfringens*. Applicants find that clays or clay formulations may bind clostridial toxins in vitro and that clays or clay formulations may alleviate disease caused by *Clostridium perfringens*, and likely other clostridial caused diseases.

Applicants also found that clays can adsorb exotoxin produced by *Clostridium difficile* and *Clostridium perfringens*. A blend that is a combination of clay, a yeast product, and a form of a functional amino acid, was found to help decrease the effects of Necrotic Enteritis in broilers when a challenge model that included *C. perfringens* and coccidia (*Eimeria maxima*) was used.

The present invention relates to an anti-toxin, an immunomodulator and a component that provides energy to mucosal cells, or a combination thereof. Advantageously, the anti-toxin may be a clay, an immunomodulator may be a yeast product and a component that provides energy to cells may be a functional amino acid such as a glutamate. In a particular advantageous embodiment, the clay may be a calcium montmorillonite clay, the yeast product may be a *Pichia guilliermondii* yeast product, and the functional amino acid may be monosodium glutamate ("MSG"). In another advantageous embodiment, the mixture may comprise about 50 to 90% (w/w) of an anti-toxin, about 10 to 50% (w/w) of an immunomodulator which may be a yeast product and about 0.01 to 15% (w/w) of a glutamate.

In a particularly preferred embodiment, the composition or mixture may be about 80% (w/w) clay, about 10% (w/w) of a yeast product and about 10% (w/w) of a glutamate or 60% (w/w) clay, about 35% (w/w) of a yeast product and about 5% (w/w) to about 10% (w/w) of a glutamate.

The present invention also encompasses the herein-disclosed compositions and/or mixtures utilized as dietary supplements. In one embodiment, the supplement may be about 0.05% (w/w) to about 0.35% (w/w) of the feed, about 0.15% (w/w) to about 0.25% (w/w) of the feed or about 0.25% (w/w) of the feed.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 18A-B depict cytokine production in the jejunum intraepithelial lymphocytes at 2 days post *C. perfringens* infection.

FIG. 18C-D depict cytokine production in the jejunum intraepithelial lymphocytes of birds at 2 days post *C. perfringens* infection.

FIGS. 19A-C depict cytokine production in the spleen of birds at 2 days post *C. perfringens* infection.

FIGS. 19D-F depict cytokine production in the spleen of birds at 2 days post *C. perfringens* infection.

DETAILED DESCRIPTION OF THE INVENTION

Figure 1:
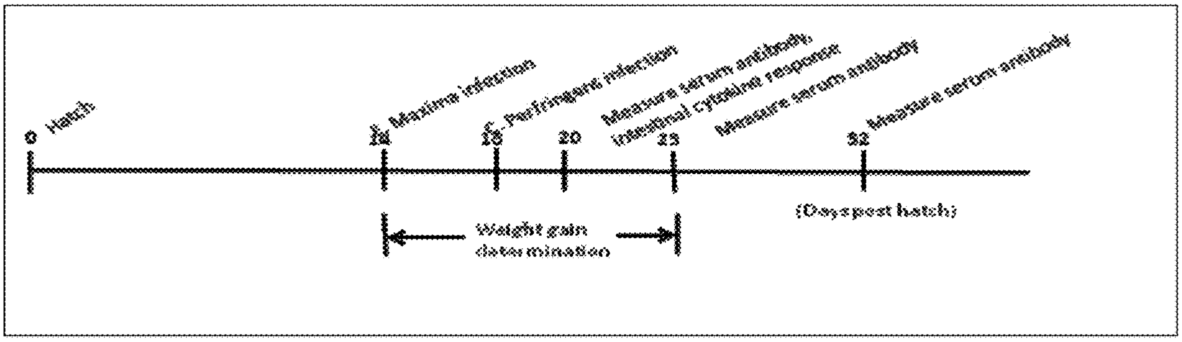
FIG. 1 depicts a schematic outline of an experimental design.

The present invention relates to an anti-toxin, an immunomodulator and a component that provides energy to mucosal cells, or a combination thereof, which may be useful for decreasing effects of Clostridial disease.

*Clostridium* is a bacterial genus that secrets toxins causing disease in poultry, animals, and humans. Applicants examined two *Clostridium* species, *Clostridium difficile* and *Clostridium perfringens*, and found that clays can adsorb exotoxin produced by both. Diseases from *C. difficile* are common in humans and pigs and disease from *C. perfringens* is common in cattle and is especially prominent in chickens and known as Necrotic Enteritis (NE). A blend that is a combination of clay, a yeast product, and a form of a functional amino acid, was examined and found to help decrease the effects of Necrotic Enteritis in broilers when a challenge model that included *C. perfringens* and coccidiosis (*Eimeria maxima*) was used.

It was previously reported that high concentrations of dietary fiber, or whole wheat diets, diets high in crude protein, especially from high concentrations of animal protein or fishmeal, or high concentrations of the amino acids glycine or methionine increased the risk of high levels of the *C. perfringens* bacteria and thus increased likelihood of necrotic enteritis (Williams, R. B. 2005 Intercurrent coccidiosis and necrotic enteritis of chickens: rational, integrated disease management by maintenance of gut integrity. Avian Path. 34:159-180). In Applicants' research, products that were a blend of a clay, a complex reduced carbon source, and an organic acid, or were an organoclay did not improve broiler performance over clay alone when challenged to induce necrotic enteritis.

Applicants conducted several in vivo experiments examining products to help alleviate necrotic enteritis. Applicants looked at the effects of six different products compared to no product or virginiamycin. In one experiment, when birds were challenged with *Clostridium perfringens* all products decreased lesion scores compared to birds challenged with *C. perfringens* that were not treated with any product. One product (Y) was equal to virginiamycin and two products (CC, B) were not significantly different than virginiamycin. When mortality was compared in birds that were challenged with *C. perfringens* only the virginiamycin was significantly better than no product, but the CC product was not significantly different than the virginiamycin. Looking at feed conversion (feed:gain) from day 14-28 (the period of time mainly affected by the *C. perfringens* challenge) two products evaluated (BFA, BT) had numerically poorer feed conversion than challenged birds with no product, while the remaining products were numerically but not significantly poorer than virginiamycin. For weight gain from day 14-28 only birds fed B had significantly higher weight gain than the birds fed no product. Because there was not a product that was consistently the best across response criteria in this experiment products were ranked by how they performed across major response criteria (Table A). This was a ranking based on the product ranking in each of four response criteria: 1) day 14-28 weight gain; 2) day 14-28 feed conversion; 3) lesion score; and 4) mortality from necrotic enteritis. There was no attempt to weight one response criteria more than another or any attempt at statistical analysis in this ranking.

TABLE A

Simple ranking of treatments based on lesion score, necrotic enteritis mortality, and d 14-28 weight gain and feed conversion ratio of birds with a *Clostridium perfringens* challenge.

| Product | Rank |
|---|---|
| Virginiamycin | 1 |
| CC | 2 |
| B | 3 |
| Y | 4 |
| CA | 5 |
| BT | 6 |
| BFA | 6 |
| No product | 7 |

Based off of the results of this and previous in vitro and in vivo work Applicants believed that clay-based products could help decrease the effects of necrotic enteritis in poultry but did not have a specific product that was obviously better than the rest. Thus, another in vivo study was conducted. In this study, the products CA, BT, and BFA were no longer used because of their ranking. Because B ranked higher than CA, the blend of CC was changed to use B and the ratio of the blend was changed for the next experiment (the new product C).

A follow-up experiment was conducted which looked at birds challenged with *C. perfringens* or *C. perfringens*+ aflatoxin. The three test products were: B, Y, or C. The three test products lessened disease. This was mainly shown in gain during the challenge period from day 10-24 in birds that had been challenged with *C. Perfringens* as the B, Y, or virginiamycin products improved gain compared to the diet with no product, with Y being statistically equal to feeding virginiamycin. With this challenge, there were no significant differences for the feed:gain ratio between products except for virginiamycin. When the necrotic enteritis challenge was coupled with the aflatoxin (1 ppm) challenge, there was more effect of products. For weight gain during the challenge period (d 14-24) birds fed any product had higher weight gain than did those fed no product. Feeding B had the most effect on gain, significantly higher than the other products including virginiamycin. The feed:gain ratio was also better for birds fed B or the C product than those fed no product (Table B).

The present invention also encompasses anti-toxins, yeasts, yeast products, or yeast-like products, and MSG-like materials in addition to the preferred embodiments disclosed herein. Other materials believed to be anti-toxins may also include other clays or minerals, yeasts or yeast products or yeast components, or yeast-like products such as other sources of fiber, beta glucans, or enzymes.

As used herein, clay may refer to any types of clay such as silicates. Silicates may include phyllosicilates, nesosilicates, cyclosilicates, sorosilicates, inosilicates and tectosilicates. Phyllosilicates may include micas, chlorites, kaolinites, smectites (bentonite clays), hormites, talcs and serpentinites. Tectosilicates may include quartz, zeolites and feldspars.

In an advantageous embodiment, the clay is a smectite (bentonite clay). Smectites include, but are not limited to trioctahedral smectites and dioctahedral smectites. Trioctahedral smectites include, but are not limited to, saponite, hectorite, stevensite and sauconite. Dioctahedral smectites include, but are not limited to, montmorillonite, beidellite and nontronite. Montmorillonite includes, but is not limited to sodium montmorillonite and calcium montmorillonite.

As used herein, yeast may refer to yeasts (such as Ascomycota and Basidiomycota), yeast fragments, yeast products or yeast-like products. In particular, the term yeast encompasses not only yeasts (such as Ascomycota and Basidiomycota), yeast fragments, yeast products or yeast-like products but also anything that may act like a yeast. As used herein, yeast may also refer to yeast product sources, or yeast fermentation products, yeast mannans, or whole yeast or components of the yeast cell (such as, but not limited to, the yeast cell wall) or mixtures of the same, or yeasts or yeast components from other species of yeast.

In an advantageous embodiment, the beta glucan may be a beta 1, 3 glucan. In another advantageous embodiment, the beta glucan may be a bacterial beta glucan or a bacterial beta 1, 3 glucan.

Other immunomodulators may also include yeasts or yeast products or yeast components, or other fibers, immunoglobulins, or sources of immunoglobulins, chitins, or corticosteroids. Other sources of energy to the gut mucosa may also include functional proteins, glutamic acid, threonine, or sources of functional protein such as plasma, or functional peptides. As used herein, peptides may be a short chain of amino acids, such as 2-4 molecules of glutamate or combinations of different amino acids with or without glutamate The present invention also involves adding heat at between 300 and 800 degrees C. for up to an hour to the clay.

The present invention also involves heating the clay, as it may impact the effectiveness of the clay. This may be done either statically using a muffle furnace or dynamically in a rotary kiln or flash dryer.

The preferred embodiment of this product may be about 50 to 90% (w/w) of an anti-toxin, such as clay, about 5 to 50% (w/w) of an immunomodulator, which may be a yeast product, and about 0.01 to 15% (w/w) of a glutamate. In an especially preferred embodiment, the product may be about 80% (w/w) of an anti-toxin, such as clay, about 10% (w/w) of an immunomodulator, which may be a yeast product, and about 10% (w/w) of a glutamate.

The anti-toxin may be a calcium montmorillonite clay, advantageously heated to a temperature at between 100-800 degrees C., advantageously between 400-800 degrees C., to decrease moisture and ground to a fine particle size. This processing, heating to between 100-800 degrees C., and/or fine grinding (with an average particle size of approximately between 20 and 50 microns) has been shown to increase the toxin binding ability of the clay across multiple toxins. The yeast product may be a *Pichia guilliermondii* or *a Saccharomyces cerevisiae* yeast product or a product from another specie of yeast. Monosodium glutamate is a form of the amino acid glutamate.

In an advantageous embodiment, the mixture may be about 80% (w/w) clay, about 30% (w/w) to about 35% (w/w) of a yeast product and about 5% (w/w) to about 10% (w/w) of a glutamate.

In a particularly advantageous embodiment, the clay may be a montmorillonite clay, preferably a highly-refined montmorillonite sorbent clay, and more preferably Calibrin®-Z. In another particularly advantageous embodiment, the yeast product may be preferably yeast mannan product. In another particularly advantageous embodiment, the glutamate is monosodium glutamate.

In a particularly preferred embodiment, the mixture may be about 60% (w/w) clay, about 30% (w/w) of a yeast product and about 10% (w/w) of a glutamate or 60% (w/w) clay, about 35% (w/w) of a yeast product and about 5% (w/w) to about 10% (w/w) of a glutamate.

In a particularly advantageous embodiment, the clay may be a montmorillonite clay, preferably a highly-refined montmorillonite sorbent clay, and more preferably Calibrin®-Z. In another particularly advantageous embodiment, the yeast product may be a yeast mannan product, including *Pichia guilliermondii* mannan products or *Saccharomyces cerevisiae* yeast products. In another particularly advantageous embodiment, the glutamate is monosodium glutamate.

The present invention also encompasses the herein-disclosed mixtures utilized as dietary supplements. In one embodiment, the supplement may be about 0.05% (w/w) to about 0.35% (w/w) of the feed, about 0.15% (w/w) to about 0.25% (w/w) of the feed or about 0.25% (w/w) of the feed.

In addition to the preferred embodiment other materials capable of binding toxins may be substituted for Amlan's products, such as other clays or sorbent minerals, diatomaceous earths, silicates, zeolites, attapulgites, hormites, or these materials or combinations of these materials (including the base material for Amlan products) manufactured with other processes (including increased or decreased drying temperature or time or final moisture content, calcined materials, or materials ground to a larger or smaller particle size) may be used with the caveat that more of the non-Amlan product may be required and/or the non-Amlan product may result in less efficacy.

The clay may be heated to about 100° C., about 125° C., about 150° C., about 175° C., about 200° C., about 225° C., about 250° C., about 275° C., about 300° C., about 325° C., about 350° C., about 375° C., about 400° C., about 425° C., about 450° C., about 475° C., about 500° C., about 525° C., about 550° C., about 575° C., about 600° C., about 625° C., about 650° C., about 675° C., about 700° C., about 725° C., about 750° C., about 775° C., about 800° C., about 825° C., about 850° C., about 875° C., about 900° C., about 925° C., about 950° C., or about 1000° C. It may be heated for 1 minute up to 4 hours.

The average particle size of the clay may be as small as 1 micron to as large as 500 microns. The average particle size may advantageously be between 20 and 50 microns.

Other yeast product sources, or yeast fermentation products, yeast mannans, or whole yeast or components of the yeast cell (such as, but not limited to, the yeast cell wall) or mixtures of the same, or yeasts or yeast components from other species of yeast may also be used. Sources for mannan oligosaccharides, and/or beta glucans, or other major components of yeast could also be used, including but not limited to, other fiber or carbohydrate sources. Other sources of prebiotics or blends of prebiotics may also be used for the present invention.

Other sources of glutamate, glutamic acid, or any of their salts, or other energy generating amino acids (including but not limited to: α-ketoglutarate, glutamine, aspartate or the branch-chain amino acids, L-glutamic acid or L-glutamine) other functional amino acids, functional peptides, or functional proteins, or nucleotides are also contemplated for the present invention.

The percent inclusion of the materials may increase or decrease from those in the preferred embodiment.

While the preferred embodiment has been shown to have value against necrotic enteritis induced by esophageal inoculation with coccidiosis (*Eimeria maxima*) and *Clostridium perfringens*, it could have similar effects against other *Clostridia* sp. or coccidia sp based diseases or other enteric diseases or by generally improving gastro intestinal health or function in any poultry species, or other species such as dogs, cats, pigs, cattle, sheep, goats, horses, and humans and aquatic species such as shrimp or farmed fish. Other possible diseases helped could be *Clostridia difficile* infection of man and animal, chronic bowel disease of man, hemorrhagic bowel disease of cows, enterotoxcimia of calves, pigs and sheep, shigalosis of man and animal, or travelers diarrhea, or other diseases caused by bacterial or food and or water borne endotoxin or exotoxins of animal or man.

A study was conducted to examine the effects of several products on the clinical signs of necrotic enteritis in broiler chickens. The products included some that Applicants had previously tested and a new combination product that Applicants had not used previously in animals. The previously tested products were: 1) a 100% clay product, (B); 2) the clay product blended with an organic acid and a plant extract (Y); 3) a blend of the clay and a yeast product (C). The previously untested product was a blend of the clay, the yeast product, and monosodium glutamate (D). These products were all tested at two concentrations, 0.25% and 0.5% of the diet. Virginiamycin (22 ppm), an antibiotic that is commonly used to prevent necrotic enteritis in poultry was also included as a treatment for comparison.

Chickens fed the diet supplemented with a combination of clay, a yeast product, and monosodium glutamate and co-infected with *E. maxima* and *C. perfringens* to induce necrotic enteritis showed significantly increased body weight gain, reduced lesion score, enhancement of the serum antibody levels to α-toxin or NetB toxin, and decreased serum α-toxin levels. This was not only significantly better compared to no product but often better compared to other tested products.

Generally, the addition of D at 0.25% of the diet showed better performance than D at 0.5% of the diets, this indicates that there is a need to balance these ingredients to provide the optimal response.

Incorporation of the clay, yeast product and optionally, glutamate, mixture of the present invention into an animal feed or water this may be done in a manner known to one of skill in the art. In a preferred embodiment, the clay, yeast product and optionally, glutamate, mixture of the invention is incorporated in a premix. The premix preferably includes the clay, yeast product and optionally, glutamate, mixture, a physiologically acceptable carrier and optionally a feedstuff. The premix is generally in a relatively concentrated form and is adapted to be diluted with other material such as one or more of the other carriers, vitamins and mineral supplements and feedstuff to form the final animal feed. The premix preferably includes the clay, yeast product and optionally, glutamate, mixture in a concentration in the range of from 0.1 to 70% by weight, preferably 0.5 to 50% by weight, more preferably about 0.25% by weight. The optimum concentration will depend on whether the treatment is preventative, for control or remedial and whether the clay, yeast product and optionally, glutamate, mixture of the invention is the only active or whether it is used in concomitant therapy with other materials and the specie and age or stage of life of the recipient.

In a preferred embodiment the concentrated composition of the clay, yeast product and optionally, glutamate, mixture is in a controlled-release form. The controlled release form will include the clay, yeast product and optionally, glutamate, mixture and a polymeric material for providing controlled release of the clay, yeast product and optionally, glutamate, mixture from the controlled-release system and is particularly useful in compositions for addition to solid feed material. As a result of the controlled release formulation the release of the clay, yeast product and optionally, glutamate, mixture may be delayed so as to occur mainly in the duodenum. A controlled release polymer may also minimize rejection of the composition due to taste or be used for rectal suppositories.

In this invention, the term, "controlled release system" is used in the same context as that in, and includes the same range of examples as quoted in "Controlled Drug Delivery" (Robinson & Lee, 1987). Many other pH-sensitive controlled-release systems which are known in the art (Robinson and Lee, 1987) may be substituted for the polymer of acrylic acid or copolymer of acrylamide and acrylic acid. For example, soluble and anionic, or insoluble cross-linked and anionic, cellulosic systems; or soluble and anionic, or insoluble cross-linked and anionic polymers derived from any generic acrylic acid polymer and/or its derivatives. Such cross-linked and insoluble polymers are preferred since they swell and also are less likely to be metabolized.

The invention also provides an animal feed composition comprising the clay, yeast product and optionally, glutamate, mixture of the invention and a feedstuff. The clay, yeast product and optionally, glutamate, mixture is preferably present in an amount of from 0.0001 to 25% of the total feed composition and preferably from 0.0001 to 5% of the total feed composition, more preferably about 0.25% of the total feed composition.

In another preferred embodiment, the clay, yeast product and optionally, glutamate, mixture of the invention may be formulated for addition to the drinking water of animals.

The clay, yeast product and optionally, glutamate, mixture of the invention is preferably administered in amounts of from 0.05 to 5000 mg/kg of body weight/day more preferably from 100 to 1000 mg/kg/day.

Examples of suitable inert carriers for use in compositions for administration of the clay, yeast product and optionally, glutamate, mixture of the invention include, but are not limited to, water, olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, polyvinyl alcohol, partially hydrolyzed polyvinyl acetate and mixtures thereof.

Solid forms for oral or rectal administration may contain pharmaceutically or veterinarally acceptable binders, sweeteners, disintegrating agents, diluents, flavorings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose or flavonoid glycosides such as neohesperidine dihydrochalcone. Suitable disintegrating agents may include corn starch, methylcellulose, polyvinlypyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange or raspberry flavorings. Suitable coating agents include polymers or copolymers of acrylic acid and/or methacrylic acid and/or their esters, and/or their amides, waxes, fatty alcohols, zein, shellac or gluten. Suitable preservatives include sodium benzoate, vitamin E, .alpha.-tocopherol, ascorbic acid, methyl parabens, propyl parabens or sodium bisulphate. Suitable lubricants include magnesium stearate, stearic acid, sodium oleate, sodium chloride or talc. Suitable time delay agents include glyceryl monostearate or glyceryl distearate.

Suspensions for oral or rectal administration may further comprise dispersing agents and/or suspending agents. Suitable suspending agents include sodium carboxylmethylcellulose, methylcellulose, hydroxypropylmethylcellulose, poly-vinyl-pyrrolidone, sodium alginate or cetyl alcohol. Suitable dispersing agents include lecithin, polyoxyethylene esters or fatty acids such as stearic acid, polyoxyethylene sorbitol mono- or di-oleate, -stearate or -laurate, polyoxyethylene sorbitan mono- or di-oleate, -stearate or -laurate and the like.

The composition of the clay, yeast product and optionally, glutamate, mixture may further comprise one or more emulsifying agents. Suitable emulsifying agents include dispersing agents as exemplified above or natural gums such as gum acacia or gum tragacanth.

Compositions for administration in the method of the invention may be prepared by means known in the art for the preparation of compositions (such as in the art of veterinary and pharmaceutical compositions) including blending, grinding, homogenizing, suspending, dissolving, emulsifying, dispersing and where appropriate, mixing of the active ingredients together with selected excipients, diluents, carriers and adjuvants.

For oral administration, the pharmaceutical or veterinary composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

TABLE B

Interaction of treatment effect of broilers fed a challenge from *Clostridium perfringens* pathogen (CPP) without and with Aflatoxin and products intended to decrease the challenge effects[1,2,3].

| | Feed intake, g | | | Gain, g | | | Feed Conversion Ratio | | | Mortality, % | | Lesions |
|---|---|---|---|---|---|---|---|---|---|---|---|---|
| | Day | | | | | | | | | | | |
| | 0-10 | 10-24 | 0-24 | 0-10 | 10-24 | 0-24 | 0-10 | 10-24 | 0-24 | 0-10 | 10-24 | 20 |
| | | | | | | No Challenge | | | | | | |
| None | $21.8^{bc}$ | $70.5^{cd}$ | $49.4^{ab}$ | $163^{cdef}$ | $783^{abc}$ | $946^{bc}$ | $1.36^{a}$ | $1.38^{de}$ | $1.38^{abcd}$ | $5.63^{bcde}$ | $0^{c}$ | $0.075^{b}$ |
| B | $21.3^{cd}$ | $71.3^{bcd}$ | $49.7^{ab}$ | $159^{cdefg}$ | $780^{abc}$ | $939^{bc}$ | $1.35^{a}$ | $1.38^{de}$ | $1.38^{abcd}$ | $7.5^{bcd}$ | $0.63^{bc}$ | $0.125^{b}$ |
| Y | $21.91^{bc}$ | $71.1^{bcd}$ | $49.7^{ab}$ | $164^{cdef}$ | $790^{ab}$ | $954^{ab}$ | $1.35^{a}$ | $1.37^{e}$ | $1.36^{de}$ | $3.13^{def}$ | $0.63^{bc}$ | $0.025^{b}$ |
| C | $23.1^{a}$ | $70.9^{bcd}$ | $50.3^{a}$ | $166^{bc}$ | $791^{ab}$ | $958^{ab}$ | $1.41^{a}$ | $1.36^{e}$ | $1.37^{cd}$ | $13.13^{a}$ | $0.63^{bc}$ | $0.050^{b}$ |
| VM | $22.6^{ab}$ | $72.2^{abc}$ | $50.5^{a}$ | $180^{a}$ | $804^{a}$ | $983^{a}$ | $1.28^{b}$ | $1.36^{e}$ | $1.34^{ef}$ | $0^{f}$ | $0.63^{bc}$ | $0.125^{b}$ |
| | | | | | | CPP Challenge | | | | | | |
| None | $19.9^{efg}$ | $69.9^{d}$ | $48.0^{c}$ | $165^{cde}$ | $730^{d}$ | $895^{d}$ | $1.23^{b}$ | $1.40^{cd}$ | $1.37^{cd}$ | $5^{cdef}$ | $2.5^{abc}$ | $0.950^{a}$ |
| B | $20.5^{def}$ | $71.5^{bcd}$ | $49.6^{ab}$ | $162^{cdef}$ | $766^{bc}$ | $928^{bc}$ | $1.28^{b}$ | $1.41^{be}$ | $1.39^{abc}$ | $10.63^{ab}$ | $3.75^{a}$ | $1.075^{a}$ |
| Y | $20.3^{def}$ | $72.6^{ab}$ | $49.9^{ab}$ | $162^{cdef}$ | $784^{abc}$ | $946^{bc}$ | $1.27^{b}$ | $1.40^{cd}$ | $1.37^{bcd}$ | $3.75^{cdef}$ | $0.63^{bc}$ | $1.250^{a}$ |
| C | $19.9^{efg}$ | $71.0^{bcd}$ | $48.7^{bc}$ | $159^{cdefg}$ | $757^{cd}$ | $916^{cd}$ | $1.28^{b}$ | $1.40^{cd}$ | $1.37^{cd}$ | $4.38^{cdef}$ | $1.25^{abc}$ | $1.025^{a}$ |
| VM | $20.9^{cde}$ | $73.6^{a}$ | $50.5^{a}$ | $174^{ab}$ | $806^{a}$ | $980^{a}$ | $1.22^{b}$ | $1.36^{e}$ | $1.33^{f}$ | $0.63^{ef}$ | $0.63^{bc}$ | $1.025^{a}$ |
| | | | | | | CPP + AFL Challenge | | | | | | |
| None | $19.0^{g}$ | $57.2^{g}$ | $40.8^{f}$ | $157^{fg}$ | $584^{g}$ | $740^{g}$ | $1.23^{b}$ | $1.45^{a}$ | $1.40^{ab}$ | $10.63^{ab}$ | $1.25^{abc}$ | $1.175^{a}$ |
| B | $19.9^{efg}$ | $65.2^{e}$ | $45.6^{d}$ | $159^{defg}$ | $695^{e}$ | $853^{e}$ | $1.28^{b}$ | $1.40^{cd}$ | $1.37^{cd}$ | $6.88^{bcd}$ | $1.25^{abc}$ | $0.975^{a}$ |
| Y | $19.9^{fg}$ | $61.1^{f}$ | $43.3^{e}$ | $157^{efg}$ | $636^{f}$ | $793^{f}$ | $1.28^{b}$ | $1.43^{ab}$ | $1.40^{ab}$ | $8.75^{abc}$ | $1.25^{abc}$ | $1.025^{a}$ |

TABLE B-continued

Interaction of treatment effect of broilers fed a challenge from *Clostridium perfringens* pathogen (CPP) without and with Aflatoxin and products intended to decrease the challenge effects[1,2,3].

| | Feed intake, g | | | Gain, g | | | Feed Conversion Ratio | | | Mortality, % | | Lesions |
|---|---|---|---|---|---|---|---|---|---|---|---|---|
| | Day | | | | | | | | | | | |
| | 0-10 | 10-24 | 0-24 | 0-10 | 10-24 | 0-24 | 0-10 | 10-24 | 0-24 | 0-10 | 10-24 | 20 |
| C | $19.0^{g}$ | $62.0^{f}$ | $43.4^{e}$ | $153^{g}$ | $647^{f}$ | $800^{f}$ | $1.27^{b}$ | $1.42^{bc}$ | $1.39^{abc}$ | $8.75^{abc}$ | $3.13^{ab}$ | $0.900^{a}$ |
| VM | $20.0^{efg}$ | $58.7^{g}$ | $41.7^{f}$ | $166^{cd}$ | $622^{f}$ | $788^{f}$ | $1.22^{b}$ | $1.43^{ab}$ | $1.38^{abcd}$ | $0.63^{ef}$ | $0.63^{bc}$ | $1.150^{a}$ |
| P < | 0.0241 | 0.001 | 0.001 | 0.299 | 0.001 | 0.001 | 0.552 | 0.003 | 0.043 | 0.024 | 0.509 | 0.962 |
| SE | 0.513 | 0.967 | 0.639 | 3.9 | 15.4 | 16.7 | 0.336 | 0.013 | 0.012 | | | |

[a-h]Means within a main effect within a column with no common superscripts differ significantly ($P < 0.05$).

[1]Means were the average of 8 replicate pens with 22 birds initially (equalized to 20 on d-7); 5 birds/pen were euthanized on d-20 for lesion scoring.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1: Summary of Clostridial Toxins/Disease, Prototype Product Efficacy

Several toxin adsorbents against 2 *Clostridium* spp. were tested in vitro and in vivo.

An in vitro adsorption assay with alpha-toxin was conducted with three samples of pulverized clays: a calcium bentonite (CBEN), an attapulgite-type Fullers Earth (AFE), and a heat treated Fullers Earth (HTF). Alpha-toxin is produced by *C. perfringens*, in the intestines of poultry during stressed conditions, resulting in necrotic enteritis. Five levels of toxin (0, 5, 10, 50, & 100 μg/ml) and three levels of each clay (0, 0.5%, & 1.0%) were tested together in 50 μl of phosphate buffer solution, incubated, centrifuged, and binding was determined by measuring hydrolysis of egg yolk lecithin agar resulting from the unbound alpha-toxin. All the products bound the toxin at some level. Table 1 shows summary results Decreasing the binder to toxin ratio resulted in separation of binding efficiencies of the clays, with CBEN having greater binding efficiency than the other two clays (approximately 2 times more efficient). Overall, the alpha-toxin in vitro binding was best for CBEN, followed by AFE, and HTF.

TABLE 1

Adsorption of *C. perfringens* Alpha Toxin
Percent alpha-toxin bound at different toxin and clay levels

| | Alpha-toxin concentration | | | |
|---|---|---|---|---|
| | 5 μg/ml | 10 μg/ml | 50 μg/ml | 100 μg/ml |
| 0.5% Clay | | | | |
| CBEN | 100 | 100 | 29 | 9 |
| AFE | 0 | 0 | 0 | 0 |
| HTF | 100 | 36 | 23 | 9 |
| Binder:toxin | 1000:1 | 500:1 | 100:1 | 50:1 |
| 1.0% Clay | | | | |
| CBEN | 100 | 100 | 78 | 34 |
| AFE | 31 | 13 | 10 | 9 |

TABLE 1-continued

Adsorption of *C. perfringens* Alpha Toxin
Percent alpha-toxin bound at different toxin and clay levels

| | Alpha-toxin concentration | | | |
|---|---|---|---|---|
| | 5 μg/ml | 10 μg/ml | 50 μg/ml | 100 μg/ml |
| HTF | 100 | 100 | 48 | 27 |
| Binder:toxin | 2000:1 | 1000:1 | 200:1 | 100:1 |

Several clays were tested for activity against 2 *C. difficile* toxins A and B (AFE, an acid-treated attapulgite (ATA), CBEN, and a heat treated calcium bentonite (HCBN). Both the clays (as fine powders) and the toxins (Purified toxins were diluted to final concentrations of 2000 cytotoxicity units per ml for toxin A and 10,000 cytotoxicity units per ml for toxin B.) were added at several different concentrations. Clays were put in a suspension with toxin and incubated. Solids were then removed by centrifugation. The supernatant (liquid leftover, where still active toxin would remain) was added to a cell culture (Chinese Hamster Ovary cells) and damage recorded. More cell damage meant less clay activity. Less cell damage meant more activity against the toxin.

Results: No product adsorbed Toxin B (which was used at 10× the rate of Toxin A). Table 2 gives example data. AFE and an ATA adsorbed some Toxin A. The following table provides an example of the results. A 100 means there was no measured lessening of toxin adsorption. A 0 means there was no toxin activity.

TABLE 2

Adsorption of *C. difficile* Toxin A and B

| attapulgite-type Fullers Earth | | Toxin A | | | | Toxin B | | | |
|---|---|---|---|---|---|---|---|---|---|
| (AFE) | | Clay dilution | | | | | | | |
| Toxin dilution | | 1:10 1 | 1:20 2 | 1:30 3 | 1:40 4 | 1:10 7 | 1:20 8 | 1:30 9 | 1:40 10 |
| 1:2 | A | 25 | 100 | 100 | 100 | 100 | 100 | 100 | 100 |
| 1:2 | B | 25 | 100 | 100 | 100 | 100 | 100 | 100 | 100 |
| 1:4 | C | 0 | 100 | 100 | 100 | 100 | 100 | 100 | 100 |
| 1:4 | D | 0 | 100 | 100 | 100 | 100 | 100 | 100 | 100 |
| 1:8 | E | 0 | 25 | 100 | 100 | 100 | 100 | 100 | 100 |
| 1:8 | F | 0 | 25 | 100 | 100 | 100 | 100 | 100 | 100 |

TABLE 2-continued

| Adsorption of *C. difficile* Toxin A and B | | | | | | | | | |
|---|---|---|---|---|---|---|---|---|---|
| atta-pulgite-type Fullers Earth | | Toxin A | | | | Toxin B | | | |
| (AFE) | | Clay dilution | | | | | | | |
| Toxin dilution | | 1:10 1 | 1:20 2 | 1:30 3 | 1:40 4 | 1:10 7 | 1:20 8 | 1:30 9 | 1:40 10 |
| 1:16 | G | 0 | 0 | 100 | 100 | 100 | 100 | 100 | 100 |
| 1:16 | H | 0 | 0 | 100 | 100 | 100 | 100 | 100 | 100 |

A follow-up round of testing using only Toxin B, where 2% clay was used and the toxins quantified by weight (not cytotoxicity units) showed that all the products tested had activity to some degree (Table 3). In this table, the definition of activity is reversed from that of Table 2. A 100 means there was no toxin activity. A 0 means there was much toxin activity (i.e. cytotoxicity).

TABLE 3

| Adsorption of *C. difficile* Toxin B, University of Arizona, 2010 | | | | | | | |
|---|---|---|---|---|---|---|---|
| Binder (%) | Toxin B Concentration (µg/mil) | | | | | | |
| 2 | 0.0977 | 0.0488 | 0.0244 | 0.0122 | 0.0061 | 0.0031 | 0.0015 |
| CBEN | 0 | 0 | 10 | 50 | 100 | 100 | 100 |
| HCBEN | 0 | 0 | 50 | 100 | 100 | 100 | 100 |
| AFE | 0 | 0 | 0 | 10 | 50 | 100 | 100 |
| ATA | 0 | 0 | 50 | 100 | 100 | 100 | 100 |
| Toxin only | 0 | 0 | 0 | 0 | 25 | 75 | 100 |
| Binder:Toxin | 204,800 | 409,600 | 819,200 | 1,638,400 | 3,276,800 | 6,553,600 | 13,107,200 |

For in vivo studies, strain JGS4143, a virulent NE field strain, was used for challenge. Newly-hatched Cornish× Rock chicks were fed an antibiotic-free chick starter diet with 16% protein for 7 days. On day 8, the diet was changed to a wheat-based, high protein (28%) feed containing 60% fishmeal and zinc at 400 ppm. Clays HCBEN, CBEN, and CBEN+probiotic were added at 1% or 2% to the feed of individual groups Before challenge (Day 14), feed was withdrawn for 20 h. Beginning on day 15, birds were fed (every 12 h for 3.5 days) a 1.25:1 feed: culture mixture. Surviving birds were necropsied on the days 18 and 19). Gross lesions were counted and scored, and duplicate specimens were collected fresh for bacteriologic culture and fixed in 10% phosphate-buffered formalin for histopathology. Paraffin-embedded tissues were sectioned (5 µm), stained with hematoxylin and eosin, examined by light microscopy, and assigned lesion scores based on the degree of necrosis. For semi-quantitative bacteriological results, segments of jejunum collected from necropsied chicks were opened aseptically on sterile foil and the mucosa removed by scraping with sterile microscope slides. Scrapings from areas with gross lesions were streak-plated on tryptose blood agar. All colonies with typical morphology and hemolytic pattern were streaked for isolation on blood agar and confirmed as *C. perfringens* (Gram-positive, anaerobic rods with double-zone hemolysis). Estimates of *C. perfringens* concentration were done by rating the colonies from sequential streaks (e.g. a 4 represents colonies on streak 4).

Results: Both clays without the probiotic showed a significant reduction of either lesion score or plate score. Chickens were all quite diseased, which was suspected to be due to the heavy inoculum and feed used.

TABLE 4

| Necrotic Enteritis in vivo results<br>Lesion and plate scores from Necrotic Enteritis in vivo chicken study* | | | | | |
|---|---|---|---|---|---|
| Clay | *Clostridium Perfringens* | # Birds Necropsied | Treatment Mortality** | Lesion Score | Plate Score |
| None | No | 10 | 29% | $0.10^{c}$ | $0.30^{c}$ |
| None | Yes | 11 | 27% | $2.14^{a}$ | $4.00^{a}$ |
| 1% CBEN | Yes | 12 | 20% | $1.83^{ab}$ | $3.17^{b}$ |
| 1% HCBEN | Yes | 14 | 7% | $1.76^{b}$ | $3.64^{ab}$ |
| 1% CBEN + Probiotic | Yes | 11 | 31% | $1.96^{ab}$ | $3.64^{ab}$ |

TABLE 4-continued

| Necrotic Enteritis in vivo results<br>Lesion and plate scores from Necrotic Enteritis in vivo chicken study* | | | | | |
|---|---|---|---|---|---|
| Clay | *Clostridium Perfringens* | # Birds Necropsied | Treatment Mortality** | Lesion Score | Plate Score |
| 2% CBEN | Yes | 9 | 31% | $1.94^{ab}$ | $3.78^{a}$ |
| 2% HCBEN | Yes | 11 | 31% | $1.95^{ab}$ | $3.82^{a}$ |
| 2% CBEN + Probiotic | Yes | 9 | 44% | $2.06^{ab}$ | $3.78^{a}$ |

*Different letters are significantly different at the p = 0.05 level.
**Treatment mortality is percent of birds that died during the *clostridium* treatment, not including those that died before *clostridium* treatment.

Since no coccidia were used in disease development (necrotic enteritis is associated with coccidial infection), a study was performed using a coccidial model.

Method: Twelve treatments (TRT) with 8 replications of 8 birds were used in an experiment to evaluate the effects of different products on gut health, growth performance, and the effects of necrotic enteritis (NE) in chickens. Six products were evaluated with a *Clostridium perfringens* challenge and two of these products were also evaluated without a *Clostridium perfringens* (CP) challenge. Chickens were fed treatment diets from 0-28 day of age with all birds receiving an oral coccidia challenge on day 14 with a mixed coccidia inoculum (~5000 oocysts of *E. maxima* per bird). Challenged birds also received a broth culture of CP ($10^8$ cfu/ml) to induce NE on d 19, 20, and 21.

Treatments are listed in Table 5.

TABLE 5

Treatments for Necrotic Enteritis Study
Treatments and description

| Trt | Trt Description | Medicated | Challenge cocci | Challenge CP | Product | Product description |
|---|---|---|---|---|---|---|
| T1 | Nonmedicated | No | Yes | No | | No product |
| T2 | Product 5 | No | Yes | No | Y | LVM + organic acid + plant extract |
| T3 | Product 6 | No | Yes | No | CC | RVM + yeast product |
| T4 | Virginamycin 20 g/t, | Yes | Yes | No | | No product |
| T5 | Nonmedicated | No | Yes | Yes | | No product |
| T6 | Product 1 | No | Yes | Yes | PA | RVM |
| T7 | Product 2 | No | Yes | Yes | B | LVM |
| T8 | Product 3 | No | Yes | Yes | BT | LVM + organic acid |
| T9 | Product 4 | No | Yes | Yes | BFA | LVM + carbon source + organic acid |
| T10 | Product 5 | No | Yes | Yes | Y | LVM + organic acid + plant exptract |
| T11 | Product 6 | No | Yes | Yes | CC | RVM + yeast product |
| T12 | Virginamycin 20 g/t | Yes | Yes | Yes | | No product |

Results: All the products reduced disease in some fashion, depending on the measurement. Table 6 shows a ranked order of performance. While virginiamycin (the drug used to control necrotic enteritis) was numerically the best, the clay products generally were not significantly different from it.

TABLE 6

Simple ranking of treatments based on lesion score, necrotic enteritis mortality, and d 14-28 weight gain and feed conversion ratio of birds with or without a *clostridium perfringens* challenge[a].

| Treatment | Rank |
|---|---|
| 4. | 1 |
| 2. | 2 |
| 3. | 2 |
| 1. | 3 |
| 12. | 4 |
| 11. | 5 |
| 7. | 6 |
| 10. | 7 |
| 6. | 8 |
| 8. | 9 |
| 9. | 9 |
| 5. | 10 |

[a]This was a ranking based on ranking in each of four response criteria: 1) d14-28 weight gain; 2) d14-28 feed conversion; 3) lesion score; and 4) mortality from necrotic enteritis. There was no attempt to weight one response criteria more than another nor any attempt at statistical analysis.

Since the number of parameters measured and the results are somewhat complicated, the following Tables merely list them.

TABLE 7

Lesion score and necrotic enteritis mortality in birds.

| Treatment | Lesion Score[b] | Necrotic Enteritis Mortality, %[c] |
|---|---|---|
| 1. No Product, No CP | $0.0^{d}$ | $0.0^{c}$ |
| 2. Product 5, No CP | $0.0^{d}$ | $0.0^{c}$ |
| 3. Product 6, No CP | $0.0^{d}$ | $0.0^{c}$ |
| 4. Virginiamycin, No CP | $0.0^{d}$ | $0.0^{c}$ |
| 5. No Product, CP | $0.8^{a}$ | $15.6^{a}$ |
| 6. Product 1, CP | $0.5^{b}$ | $15.6^{a}$ |
| 7. Product 2, CP | $0.3^{bc}$ | $14.1^{ab}$ |

TABLE 7-continued

Lesion score and necrotic enteritis mortality in birds.

| Treatment | Lesion Score[b] | Necrotic Enteritis Mortality, %[c] |
|---|---|---|
| 8. Product 3, CP | $0.5^{b}$ | $15.6^{a}$ |
| 9. Product 4, CP | $0.5^{b}$ | $9.4^{ab}$ |
| 10. Product 5, CP | $0.1^{cd}$ | $9.4^{ab}$ |
| 11. Product 6, CP | $0.4^{bc}$ | $7.8^{abc}$ |
| 12. Virginiamycin, CP | $0.2^{cd}$ | $6.3^{bc}$ |

[a]Numbers with different letters are significant at the p = 0.05 level.

[b]Scoring was based on a 0 to 3 score, with 0 being normal and 3 being the most severe.

[c]Mortality determined to have been caused by necrotic enteritis divided by the number of birds that started the experiment (8/pen).

TABLE 8

Growth performance of birds.

| Treatment | Feed Conversion Day 0-21 | Feed Conversion Day 14-21 | Weight Gain Day 0-21 | Weight Gain Day 14-21 |
|---|---|---|---|---|
| 1. No Prod. No CP | $1.724^{cdef}$ | $1.650^{bcd}$ | $0.560^{abc}$ | $0.308^{abc}$ |
| 2. Product 5, No CP | $1.688^{def}$ | $1.581^{cd}$ | $0.589^{a}$ | $0.327^{a}$ |
| 3. Product 6, No CP | $1.644^{f}$ | $1.627^{bcd}$ | $0.597^{a}$ | $0.317^{ab}$ |
| 4. Virginiamycin, No CP | $1.676^{ef}$ | $1.550^{d}$ | $0.569^{ab}$ | $0.325^{a}$ |
| 5. No Prod, CP | $1.844^{ab}$ | $1.828^{a}$ | $0.512^{bcd}$ | $0.271^{d}$ |
| 6. Product 1, CP | $1.800^{abc}$ | $1.621^{bcd}$ | $0.493^{d}$ | $0.283^{cd}$ |
| 7. Product 2, CP | $1.769^{abcde}$ | $1.731^{abc}$ | $0.519^{bcd}$ | $0.281^{d}$ |
| 8. Product 3, CP | $1.763^{abcde}$ | $1.811^{a}$ | $0.563^{abc}$ | $0.288^{cd}$ |
| 9. Product 4, CP | $1.723^{cdef}$ | $1.809^{a}$ | $0.540^{abcd}$ | $0.289^{cd}$ |
| 10. Product 5, CP | $1.787^{abcd}$ | $1.638^{bcd}$ | $0.503^{cd}$ | $0.288^{cd}$ |
| 11. Product 6, CP | $1.855^{a}$ | $1.752^{ab}$ | $0.508^{bcd}$ | $0.282^{d}$ |
| 12. Virginiamycin, CP | $1.746^{bcdef}$ | $1.566^{d}$ | $0.511^{bcd}$ | $0.295^{bcd}$ |

| Treatment | Feed Conversion Day 0-28 | Feed Conversion Day 14-28 | Weight Gain Day 0-28 | Weight Gain Day 14-28 |
|---|---|---|---|---|
| 1. No Prod. No CP | $1.652^{cde}$ | $1.567^{bcd}$ | $0.792^{ab}$ | $0.540^{abcd}$ |
| 2. Product 5, No CP | $1.637^{de}$ | $1.540^{cd}$ | $0.805^{ab}$ | $0.544^{abcd}$ |
| 3. Product 6, No CP | $1.617^{e}$ | $1.589^{bcd}$ | $0.844^{a}$ | $0.564^{ab}$ |
| 4. Virginiamycin, No CP | $1.604^{e}$ | $1.480^{d}$ | $0.845^{a}$ | $0.601^{a}$ |
| 5. No Prod, CP | $1.768^{ab}$ | $1.708^{ab}$ | $0.723^{b}$ | $0.483^{d}$ |
| 6. Product 1, CP | $1.809^{a}$ | $1.676^{abc}$ | $0.723^{b}$ | $0.512^{bcd}$ |
| 7. Product 2, CP | $1.720^{bcd}$ | $1.652^{bc}$ | $0.799^{ab}$ | $0.562^{abc}$ |

TABLE 8-continued

Growth performance of birds.

| | | | | |
|---|---|---|---|---|
| 8. Product 3, CP | 1.770$^{ab}$ | 1.826$^{a}$ | 0.771$^{ab}$ | 0.497$^{cd}$ |
| 9. Product 4, CP | 1.727$^{abc}$ | 1.832$^{a}$ | 0.747$^{b}$ | 0.496$^{d}$ |
| 10. Product 5, CP | 1.766$^{ab}$ | 1.648$^{bc}$ | 0.726$^{b}$ | 0.511$^{bcd}$ |
| 11. Product 6, CP | 1.763$^{ab}$ | 1.649$^{bc}$ | 0.772$^{ab}$ | 0.546$^{abcd}$ |
| 12. Virginiamycin, CP | 1.706$^{bcd}$ | 1.563$^{bcd}$ | 0.742$^{b}$ | 0.526$^{bcd}$ |

Example 2: The Effects of Necrotic Enteritis and Aflatoxin on Growth Performance, Lesion Scores, and Mortality in Young Broilers and Products to Alleviate them Little is known about possible necrotic enteritis/aflatoxin interactions. A study was conducted to investigate possible interactions, and the ability of several prototype products to lessen disease. The product key B=LVM clay; Y=B+organic acid+plant extract; C=B+yeast product; The 3 test materials lessened disease.

Cobb 500 chicks (2,640, male) were used to determine the effects of disease challenge and products to decrease those effects. Three challenge levels were used; 1) no challenge; 2) necrotic enteritis (CPP) challenge; and 3) CPP+1 ppm aflatoxin B1. Products tested to alleviate disease challenges were: 1) no product (NP); 2) a proprietary clay-based product (B); 3) (Y); 4) C); and 5) virginiamycin (VM). In the 24 d study, 22 chicks (equalized to 20 on d-7) per pen were allotted to 15 treatments (3×5 factorial arrangement) with 8 replications (experimental unit=pen). Significant difference was set at P<0.05. Weights were taken on d-0, 10, and 24 for calculation of feed intake, gain, and feed:gain. Birds consumed feed and water ad libitum. Increased negative responses to the combination of NE and AFL were seen in this study as Fl (d-0-10), gain (d-10-24, d-0-24), and F:G (d-10-24) were increasingly poorer as challenge level went from no-challenge to CPP challenge to CPP+AFL challenge (P<0.05). Other growth responses were worse than non- or CPP-challenges when both CPP+AFL were applied (P<0.05). Lesion score was higher in CPP challenged birds with or without AFL (P<0.05). Feeding VM improved performance in non-challenged birds (P<0.05). In CPP challenged birds, adding B or Y improved Fl and gain compared to NP; with Y being equal to those fed VM during the challenge period (P<0.05). Birds given B had the highest gain and feed conversion when challenged with both CPP and AFL; feeding Y, C, and VM had higher gains than adding NP (P<0.05). In conclusion, increasing challenge level decreased bird performance. Birds with necrotic enteritis fed Y had gain that was equal to those fed VM during the challenge period. Feeding the clay-based products improved performance during a CPP+AFL challenge.

Tables 9 and 10—Data Tables, CQR

TABLE 9

Main effect of increasing challenge from *Clostridium perfringens* pathogen (CPP) without and with Aflatoxin and five products intended to decrease the challenge effect.

| | Challenge | | | | | Products[3] | | | | | | |
|---|---|---|---|---|---|---|---|---|---|---|---|---|
| | None | CPP | CPP + AFL | P value | SE | None | B | Y | C | VM | P value | SE |
| Daily Feed Intake, g | | | | | | | | | | | | |
| 0-10 d | 22.1$^{a}$ | 20.3$^{b}$ | 19.6$^{c}$ | 0.001 | 0.230 | 20.3$^{b}$ | 20.6$^{b}$ | 20.7$^{ab}$ | 20.7$^{ab}$ | 21.2$^{a}$ | 0.046 | 0.296 |
| 10-24 d | 71.2$^{a}$ | 71.7$^{a}$ | 60.8$^{b}$ | 0.001 | 0.432 | 65.9$^{c}$ | 69.3$^{a}$ | 68.3$^{ab}$ | 68.0$^{b}$ | 68.2$^{b}$ | 0.001 | 0.558 |
| 0-24 d | 49.9$^{a}$ | 49.4$^{a}$ | 43.0$^{b}$ | 0.001 | 0.286 | 46.1$^{c}$ | 48.3$^{a}$ | 47.6$^{ab}$ | 47.5$^{b}$ | 47.6$^{ab}$ | 0.001 | 0.369 |
| Gain, g | | | | | | | | | | | | |
| 0-10 d | 166$^{a}$ | 164$^{a}$ | 158$^{b}$ | 0.001 | 1.7 | 161$^{b}$ | 160$^{b}$ | 161$^{b}$ | 159$^{b}$ | 173$^{a}$ | 0.001 | 2.2 |
| 10-24 d | 790$^{a}$ | 769$^{b}$ | 637$^{c}$ | 0.001 | 6.9 | 699$^{b}$ | 747$^{a}$ | 737$^{a}$ | 732$^{a}$ | 744$^{a}$ | 0.001 | 8.9 |
| 0-24 d | 956$^{a}$ | 933$^{b}$ | 795$^{c}$ | 0.001 | 7.5 | 860$^{c}$ | 907$^{ab}$ | 898$^{b}$ | 891$^{b}$ | 917$^{a}$ | 0.001 | 9.7 |
| FCR (F:G) | | | | | | | | | | | | |
| 0-10 d | 1.35$^{a}$ | 1.26$^{b}$ | 1.26$^{b}$ | 0.001 | 0.15 | 1.28$^{bc}$ | 1.30$^{ab}$ | 1.30$^{ab}$ | 1.32$^{a}$ | 1.24$^{c}$ | 0.001 | 0.019 |
| 10-24 d | 1.37$^{c}$ | 1.40$^{b}$ | 1.42$^{a}$ | 0.001 | 0.006 | 1.41$^{a}$ | 1.41$^{a}$ | 1.40$^{ab}$ | 1.40$^{b}$ | 1.39$^{b}$ | 0.004 | 0.008 |
| 0-24 d | 1.37$^{b}$ | 1.37$^{b}$ | 1.39$^{a}$ | 0.002 | 0.005 | 1.38$^{a}$ | 1.38$^{a}$ | 1.38$^{a}$ | 1.38$^{a}$ | 1.35$^{b}$ | 0.003 | 0.007 |
| Mortality, % | | | | | | | | | | | | |
| 0-10 d | 5.88 | 4.88 | 7.13 | 0.198 | | 7.08$^{ab}$ | 8.33$^{ab}$ | 5.21$^{b}$ | 8.75$^{a}$ | 0.42$^{c}$ | 0.001 | |
| 10-24 d | 0.50 | 1.7 | 1.50 | 0.137 | | 1.25 | 1.88 | 0.89 | 1.67 | 0.63 | 0.537 | |
| Lesion Score at d-20 | 0.080$^{b}$ | 1.065$^{a}$ | 1.045$^{a}$ | 0.001 | | 0.733 | 0.725 | 0.767 | 0.658 | 0.767 | 0.953 | |

1 From cultured material from Veterinary Medical Diagnostic Laboratory, College of Veterinary Medicine, University of Missouri, Columbia, Missouri.

2 CPP birds were challenged by being placed on dirty litter obtained from broilers that had undergone a recent *Clostridium perfringens* challenge, they were then given a 10 x dose of coccidia vaccine on d 10 to simulate conditions that cause necrotic enteritis.

[3] B = LVM clay; Y = B + organic acid + plant extract; C = B + yeast product; VM = Virginiamycin

TABLE 10

Interaction of treatment effect of broilers fed an increasing challenge from *Clostridium perfringens* pathogen (CPP) without and with Aflatoxin and 5 products intended to decrease the challenge effect.

| Challenge | None | | | | | CPP | | | | |
|---|---|---|---|---|---|---|---|---|---|---|
| Product[3] | None | B | Y | C | VM | None | B | Y | C | VM |
| AFL, ppm | | | | | | | | | | |
| Starter | —[4] | — | — | — | — | — | — | — | — | — |
| Grower | — | — | — | — | — | — | — | — | — | — |
| Feed intake | | | | | | | | | | |
| 0-10 d | $21.8^{be}$ | $21.3^{ed}$ | $21.9^{be}$ | $23.1^{a}$ | $22.6^{ab}$ | $19.9^{efg}$ | $20.5^{def}$ | $20.3^{def}$ | $19.9^{efg}$ | $20.9^{cde}$ |
| 10-24 d | $70.5^{ed}$ | $71.3^{bed}$ | $71.1^{bed}$ | $70.9^{bcd}$ | $72.2^{abe}$ | $69.9^{d}$ | $71.5^{bcd}$ | $72.6^{ab}$ | $71.0^{bcd}$ | $73.6^{a}$ |
| 0-24 d | $49.4^{ab}$ | $49.7^{ab}$ | $49.7^{ab}$ | $50.3^{a}$ | $50.5^{a}$ | $48.0^{c}$ | $49.6^{ab}$ | $49.9^{ab}$ | $48.7^{be}$ | $50.5^{a}$ |
| Gain, g | | | | | | | | | | |
| 0-10 d | $163^{edef}$ | $159^{cdefg}$ | $164^{cdef}$ | $166^{bc}$ | $180^{a}$ | $165^{cde}$ | $162^{cdef}$ | $162^{cdef}$ | $159^{cdefg}$ | $174^{ab}$ |
| 10-24 d | $763^{abc}$ | $780^{abc}$ | $790^{ab}$ | $791^{ab}$ | $804^{a}$ | $730^{d}$ | $766^{bc}$ | $784^{abc}$ | $757^{cd}$ | $806^{a}$ |
| 0-24 d | $946^{bc}$ | $939^{bc}$ | $954^{ab}$ | $958^{ab}$ | $983^{a}$ | $895^{d}$ | $928^{bc}$ | $946^{bc}$ | $916^{cd}$ | $980^{a}$ |
| FCR (F:G) | | | | | | | | | | |
| 0-10 d | $1.36^{a}$ | $1.35^{a}$ | $1.35^{a}$ | $1.41^{a}$ | $1.28^{b}$ | $1.23^{b}$ | $1.28^{b}$ | $1.27^{b}$ | $1.28^{b}$ | $1.22^{b}$ |
| 10-24 d | $1.38^{de}$ | $1.38^{de}$ | $1.37^{e}$ | $1.36^{e}$ | $1.36^{e}$ | $1.40^{cd}$ | $1.41^{bc}$ | $1.40^{cd}$ | $1.40^{cd}$ | $1.36^{e}$ |
| 0-24 d | $1.38^{abcd}$ | $1.38^{abcd}$ | $1.36^{de}$ | $1.37^{cd}$ | $1.34^{ef}$ | $1.37^{cd}$ | $1.39^{abc}$ | $1.37^{bcd}$ | $1.37^{cd}$ | $1.33^{f}$ |
| Mortality, % | | | | | | | | | | |
| 0-10 d | $5.63^{bede}$ | $7.5^{bed}$ | $3.13^{def}$ | $13.13^{a}$ | $0^{f}$ | $5^{cdef}$ | $10.63^{ab}$ | $3.75^{cdef}$ | $4.38^{cdef}$ | $0.63^{ef}$ |
| 10-24 d | $0^{e}$ | $0.63^{bc}$ | $0.63^{bc}$ | $0.63^{bc}$ | $0.63^{bc}$ | $2.5^{abc}$ | $3.75^{a}$ | $0.63^{bc}$ | $1.25^{abc}$ | $0.63^{bc}$ |
| Lesion Score | | | | | | | | | | |
| d-20 | $0.075^{b}$ | $0.125^{b}$ | $0.025^{b}$ | $0.050^{b}$ | $0.125^{e}$ | $0.950^{a}$ | $1.075^{a}$ | $1.250^{a}$ | $1.025^{a}$ | $1.025^{a}$ |

| Challenge | CPP + AFL | | | | | | |
|---|---|---|---|---|---|---|---|
| Product[3] | None | B | CY | C | VM | P< | SE |
| AFL, ppm | | | | | | | |
| Starter | 1.020 | 0.936 | 1.020 | 0.850 | 0.910 | | |
| Grower | 0.950 | 0.870 | 0.855 | 0.875 | 0.840 | | |
| Feed intake | | | | | | | |
| 0-10 d | $19.0^{g}$ | $19.9^{efg}$ | $19.9^{fg}$ | $19.0^{g}$ | $20.0^{efg}$ | 0.0241 | 0.513 |
| 10-24 d | $57.2^{g}$ | $65.2^{e}$ | $61.1^{f}$ | $62.0^{f}$ | $58.7^{g}$ | 0.001 | 0.967 |
| 0-24 d | $40.8^{f}$ | $45.6^{d}$ | $43.3^{e}$ | $43.4^{e}$ | $41.7^{f}$ | 0.001 | 0.639 |
| Gain, g | | | | | | | |
| 0-10 d | $157^{fg}$ | $159^{defg}$ | $157^{efg}$ | $153^{g}$ | $166^{cd}$ | 0.299 | 3.9 |
| 10-24 d | $584^{g}$ | $695^{e}$ | $636^{f}$ | $647^{f}$ | $622^{f}$ | 0.001 | 15.4 |
| 0-24 d | $740^{g}$ | $853^{e}$ | $793^{f}$ | $800^{f}$ | $788^{f}$ | 0.001 | 16.7 |
| FCR (F:G) | | | | | | | |
| 0-10 d | $1.23^{b}$ | $1.28^{b}$ | $1.28^{b}$ | $1.27^{b}$ | $1.22^{b}$ | 0.552 | 0.336 |
| 10-24 d | $1.45^{a}$ | $1.40^{cd}$ | $1.43^{ab}$ | $1.42^{bc}$ | $1.43^{ab}$ | 0.003 | 0.013 |
| 0-24 d | $1.40^{ab}$ | $1.37^{cd}$ | $1.40^{ab}$ | $1.39^{abc}$ | $1.38^{abcd}$ | 0.043 | 0.012 |
| Mortality, % | | | | | | | |
| 0-10 d | $10.63^{ab}$ | $6.88^{bcd}$ | $8.75^{abc}$ | $8.75^{abc}$ | $0.63^{ef}$ | 0.024 | |
| 10-24 d | $1.25^{abc}$ | $1.25^{abc}$ | $1.25^{abc}$ | $3.13^{ab}$ | $0.63^{bc}$ | 0.509 | |
| Lesion Score | | | | | | | |
| d-20 | $1.175^{a}$ | $0.975^{a}$ | $1.025^{a}$ | $0.900^{a}$ | $1.150^{a}$ | 0.962 | |

[1]Cultured material from Veterinary Medical Diagnostic Laboratory, College of Veterinary Medicine, University of Missouri, Columbia, Missouri.

[2]CPP birds were challenged by being placed on dirty litter obtained from broilers that had undergone a recent *Clostridium perfringens* challenge, they were then given a 10 x dose of coccidia vaccine on d 10 to simulate conditions that cause necrotic enteritis.

[3]B = LVM clay; Y = B + organic acid + plant extract; C = B + yeast product; VM = Virginiamycin

[4]Dashes = no Aflatoxin $B_1$ detected

Example 3: The Effects of Necrotic Enteritis and Aflatoxin on Growth Performance, Lesion Scores, and Mortality in Young Broilers and Products to Alleviate them Cobb 500 chicks (2,640, male) were used to determine the effects of disease challenge and products to decrease those effects. Three challenge levels were used; 1) no challenge; 2) necrotic enteritis (CPP) challenge; and 3) CPP+1 ppm aflatoxin $B_1$. Products tested to alleviate disease challenges were: 1) no product (NP); 2) a proprietary clay-based product (B); 3) a second proprietary clay-based product (Y); 4) a third proprietary clay-based product (C); and 5) virginiamycin (VM). In the 24 d study, 22 chicks (equalized to 20 on day7) per pen were allotted to 15 treatments (3×5 factorial arrangement) with 8 replications (experimental unit=pen). Significant difference was set at P<0.05. Weights were taken on day 0, 10, and 24 for calculation of feed intake, gain, and feed:gain. Birds consumed feed and water ad libitum. Increased negative responses to the combination of NE and AFL were seen in this study as FI (d-0-10), gain (d-10-24, d-0-24), and F:G (d-10-24) were increasingly poorer as challenge level went from no-challenge to CPP challenge to CPP+AFL challenge (P<0.05). Other growth responses were worse than non- or CPP-challenges when both CPP+AFL were applied (P<0.05). Lesion score was higher in CPP challenged birds with or without AFL (P<0.05). Feeding VM improved performance in non-challenged birds (P<0.05). In CPP challenged birds, adding B or Y improved FI and gain compared to NP; with Y being equal to those fed VM during the challenge period (P<0.05). Birds given B had the highest gain and feed conversion when challenged with both CPP and AFL; feeding Y, CL3, and VM had higher gains than adding NP (P<0.05). In conclusion, increasing challenge level decreased bird performance. Birds with necrotic enteritis fed Y had gain that was equal to those fed VM during the challenge period. Feeding the clay-based products improved performance during a CPP+AFL challenge.

Example 4: The Effects of Necrotic Enteritis, Aflatoxin, and Virginiamycin on Growth Performance, Lesion Scores, and Mortality in Young Broilers A total of 2,112, male, Cobb 500 chicks were used to determine the effects of increasing aflatoxin concentration (AFL; 0, 0.75, 1.5 ppm) on broilers with or without necrotic enteritis or virginiamycin (VM). In the 23 day study, 22 chicks (equalized to 20 on d-7) per pen were allotted to 12 treatments (3×2×2 factorial arrangement) with 8 replications in a randomized complete block design; pen was the experimental unit. Significant difference was set at P<0.05. Weights were taken on d-0, 16, and 23 for calculation of feed intake, gain, and feed:gain. Birds consumed feed and water ad libitum. Aflatoxin decreased gain and feed intake and resulted in poorer feed:gain, mortality, and lesion scores (P<0.05). Inducing necrotic enteritis (CPP) using *Clostridium perfringens* contaminated litter and a 10× dose of coccidiosis vaccine administered on day-10 increased lesion score and decreased feed intake and gain (P<0.05). Adding VM to the diets improved gain, feed intake, and feed conversion, and decreased mortality (P<0.05). However, there were interactions (P<0.05) as challenging birds in the second period with CPP and feeding 0.75 ppm AFL had a negative synergistic effect on gain while even an additive effect was not seen when birds were fed 1.5 ppm AFL. At 1.5 ppm AFL non CPP-challenged birds fed VM had higher gain that those birds not fed VM, which was equal to gain from challenged birds with or without VM. A similar interaction (P<0.05) was seen in the overall feeding period although VM helped CPP challenged birds at 0.75 ppm overall. Virginiamycin improved feed conversion with the greatest improvement at 1.5 ppm. Aflatoxin increased lesion scores in unchallenged but not in challenged birds. VM increased lesion scores in challenged but not in unchallenged birds (P<0.05). Aflatoxin and necrotic enteritis decrease broiler performance and interact to decrease weight gain; VM helps improve gain in challenged birds at 0.75 ppm AFL but not at 1.5 ppm AFL.

Example 5: Effects of the Amlan Products Against the Effects of Necrotic Enteritis in Broiler Birds The purpose of this Example was to evaluate the effect of Amlan products on NE clinical signs, immunopathology and cytokine responses in broiler chickens co-infected with *Eimeria maxima* and *Clostridium perfringens* in Necrotic Enteritis (NE) Disease Model. NE disease model used for this trial (Park S S, Lillehoj H S, et al. Immunopathology and cytokine responses in broiler chickens coinfected with *Eimeria maxima* and *Clostridium perfringens* with the use of an animal model of necrotic enteritis. Avian Diseases 2008; 52:14-22; Jang S I, Lillehoj H S, et al. Vaccination with *Clostridium perfringens* recombinant proteins in combination with Montanide™ ISA 71 VG adjuvant increase protection against experimental necrotic enteritis in commercial broiler chickens. Vaccine 2012; 30:5401-5406).

Materials and Methods.

Amlan Products were a 100% clay product (B), the clay product blended with an organic acid and a plant extract (Y), a blend of the clay and a yeast product (C), a blend of the clay, the yeast product, and monosodium glutamate (D) and the antibiotic virginiamycin (VM). The chickens were one-day-old Broiler birds (Ross/Ross) hatched at the Longeneckers Hatchery (Elizabethtown, Pa.) transported by mail truck and housed in starter brooder units. The birds were kept in brooder pens in *Eimeria*-free facility and transferred into large hanging cages in a separate location where they were infected and kept until the end of experimental period for the live challenge infection study. All procedures regarding transportation, measuring body weight, infection, and collecting blood and spleen were in accordance with established guidelines for animal experiments.

All birds were fed a non-medicated commercial basal ration of 17% crude protein from 1-18 days of age. The feed was mixed with the products B, Y, C, D, and VM respectively. At 18 days of age, the feed was replaced with commercial non-medicated feed containing 24% crude protein starter feed.

Strains of *Eimeria* spp. were maintained and propagated in accordance with established procedure. *E. maxima* (41A) were cleaned by floatation on 5% sodium hypochlorite, washed three times with PBS, and viability was enumerated by trypan blue using a hemocytometer. The oocyst number is based on only sporulated oocysts. At day 14, chickens were inoculated esophageally with 10,000 of *E. maxima* using an inoculation needle.

Four days after *Eimeria* infection, birds of NE Groups were inoculated esophageally with $1\times10^9$ CFU *Clostridium perfringens* each using an inoculation needle.

Birds were weighed just before challenge with *E. maxima* (EM), 0, and 2nd days post *C. perfringens* challenge to calculate the weight gain.

To determine a lesion score, birds (5 birds/group) were sacrificed at 2 day post *C. perfringens* (CP) infection. Approximately 20 cm intestinal segments extending 10 cm anterior and posterior to diverticulum obtained and cut longitudinally. Lesion scores were evaluated by 3 independent observers from 0 to 4 in ascending order of severity of the lesion.

On each of 0, 2, 7 and 14 days post CP infection, a total of 12 birds (5/group) were sampled for serum for antibody titers (collect individually). For sera, blood samples were obtained from individual birds (3 ml/bird), allowed to clot overnight at 4° C., and the sera were collected.

Serum samples were tested for antibodies against *clostridium* using an established ELISA. Briefly, microtiter plates were coated overnight with 200 ng/well of the recombinant *clostridium* antigen, washed with PBS-0.05% Tween, and blocked with PBS-1% BSA. Serum dilutions added, incubated with continuous gentle shaking, washed, and bound Ab detected with peroxidase-conjugated rabbit anti-chicken IgG (Sigma) and peroxidase-specific substrate. Optical density (OD) was determined at 450 nm using a microplate reader (Bio-Rad, Richmond, Calif.).

Serum samples were tested for antigens against α-toxin or NetB using an established ELISA. Briefly, microtiter plates were coated overnight with 0.5 μg/well of the mAb to α-toxin or NetB toxin, washed with PBS-0.05% Tween, and blocked with PBS-1% BSA. Chicken serum dilutions added, incubated with continuous gentle shaking, washed, and bound Ab detected with peroxidase-conjugated rabbit anti-α-toxin or NetB toxin and peroxidase-specific substrate. Optical density (OD) was determined at 450 nm using a microplate reader (Bio-Rad, Richmond, Calif.).

For statistical analysis, all values were expressed as mean±SEM. Mean values for body weight gain and lesion score were compared among groups by the Duncan's Multiple Range test following ANOVA using SPSS 15.0 for Windows (SPSS Inc., Chicago, Ill.). Differences among means were considered significant at $p<0.05$.

TABLE 11

Experimental Design

| Group # | Bird (Number) | Product | Inclusion, % | Infection for NE (EM + CP)* |
|---|---|---|---|---|
| 1 | 20 | No | — | − |
| 2 | 20 | No | — | + |
| 3 | 20 | B | 0.25 | + |
| 4 | 20 | Y | 0.25 | + |
| 5 | 20 | C | 0.25 | + |
| 6 | 20 | D | 0.25 | + |
| 7 | 20 | B | 0.5 | + |
| 8 | 20 | Y | 0.5 | + |
| 9 | 20 | C | 0.5 | + |
| 10 | 20 | D | 0.5 | + |
| 11 | 20 | VM | 22 ppm | + |

*Chickens were orally infected with $1.0 \times 10^4$ oocysts/bird of *E. maxima* (EM) at day 15 post-hatch and with $1.0 \times 10^9$ CFU/bird of *C. perfringens* (CP) at day 19.

220 broiler birds (20/group) were used and housed in brooder pens with 2 brooder Petersime per unit. The finisher unit was an 80 hanging cage unit where the birds were transferred at 18 days of age.

Chickens arrived on day 0 and moved to Petersime units the same day. The chickens were moved to large cages on day 18. Birds were infected with 10,000 sporulated oocysts of *E. maxima* at day 14 and infected with $1\times10^9$ CFU of *C. perfringens* on day 18. Blood was collected on day 14, 18, 20, 25 and 32. Lesions were scored on day 20. Body weight was determined on day 14, 20 and 25 (see, e.g., FIG. 1).

Figure 2:
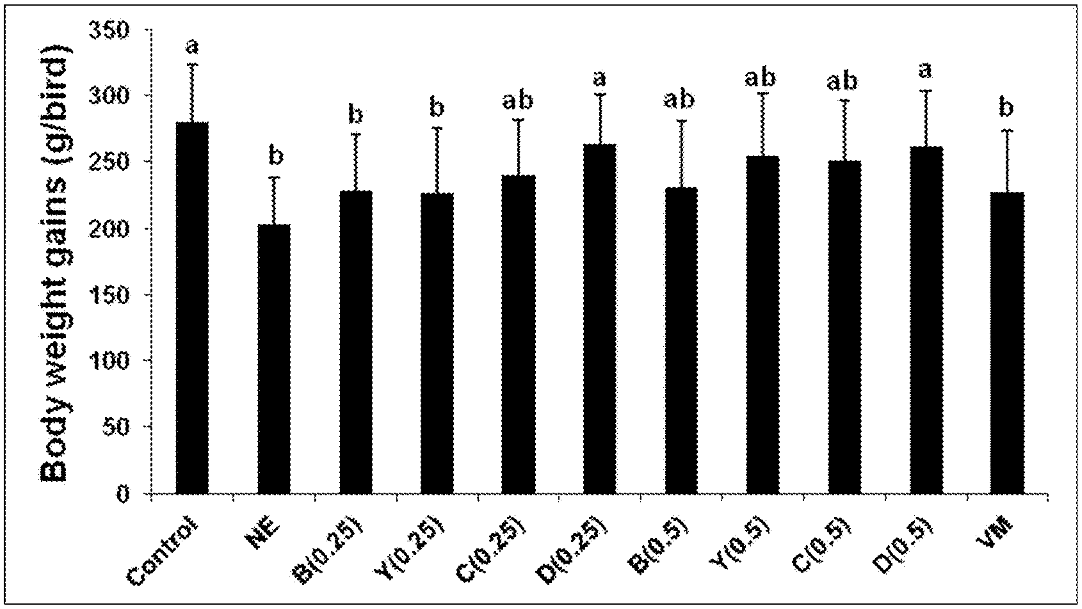
FIG. 2 depicts a comparison of the body weight gains in broiler chickens fed with Oil-Dri Corporation of America's Amlan International branded ("Amlan") products such as a 100% clay product, (B), the clay product blended with an organic acid and a plant extract (Y), a blend of the clay and a yeast product (C), a blend of the clay, the yeast product, and monosodium glutamate (D), compared to the antibiotic virginiamycin (VM) and challenged with *Clostridium perfringens* (CP) to induce necrotic enteritis. Body weights were determined from the day of *E. maxima* infection to 2 days post CP infection. Birds were infected with 10,000 sporulated oocysts of *E. maxima* at day 14 post hatch. After 4 days *E. maxima* infection, birds except those in the Control treatment were inoculated with $1\times10^9$ CFU CP.

As shown in FIG. 2, chickens were fed the 0.25% of D and 0.5% of D-supplemented diet and co-infected with *E. maxima* and *C. perfringens* exhibited increased body weight compared with the infected animals given the non-supplemented diet.

Figure 3:
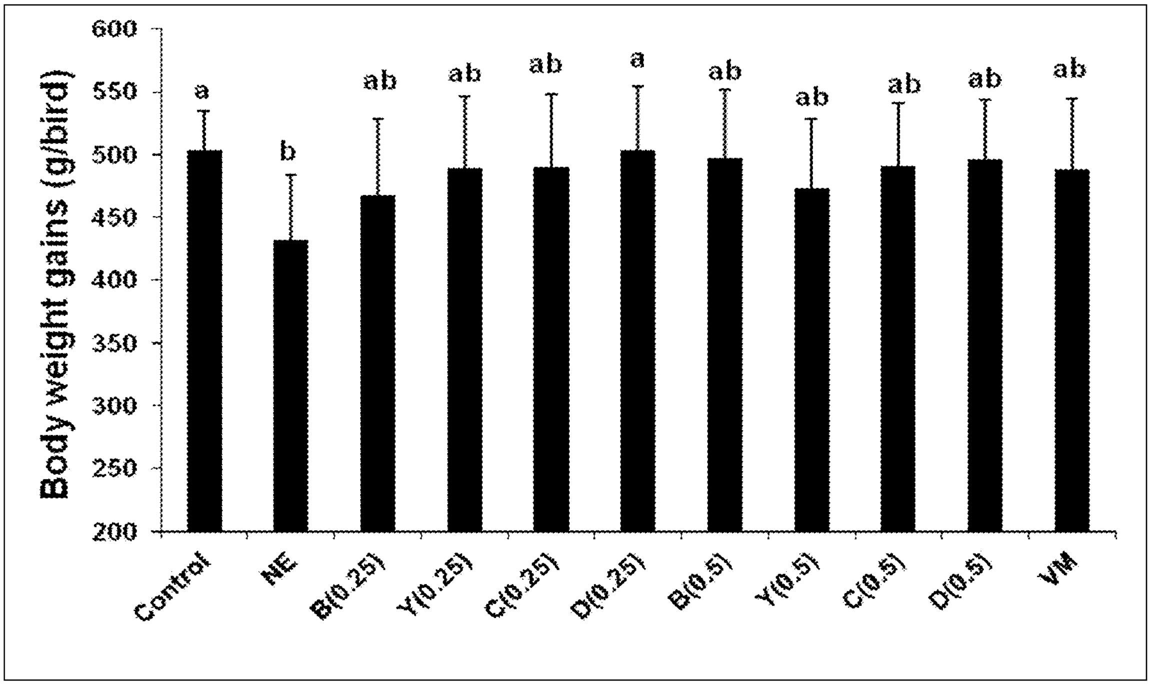
FIG. 3 depicts a comparison of the body weight gains in broiler chickens fed with Amlan products such as B, Y, C, D, and compared to the antibiotic VM. Body weight gains were determined from the day of CP infection to 7 days post CP infection. Birds were infected with 10,000 sporulated oocysts of *E. maxima* at day 14 post hatch. After 4 days *E. maxima* infection, birds were inoculated with $1\times10^9$ CFU CP.

As shown in FIG. 3, chickens fed the 0.25% of D-supplemented diet and co-infected with *E. maxima* and *C. perfringens* exhibited increased body weight compared with the infected animals given the non-supplemented diet (control NE group).

Figure 4:
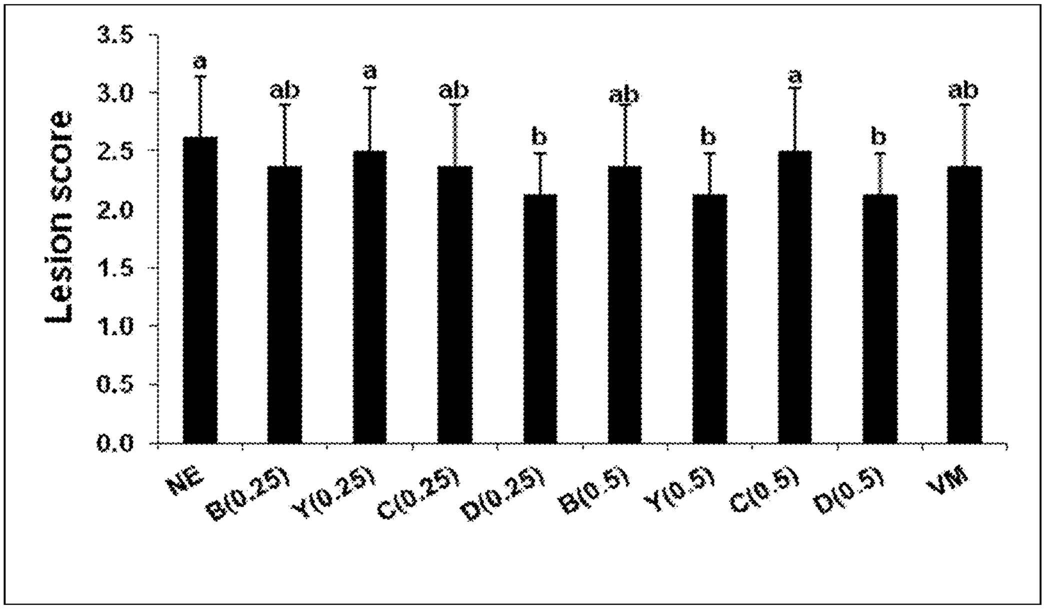
FIG. 4 depicts an effect of dietary Amlan products on intestinal lesion scores.

As shown in FIG. 4, birds fed with D (0.25%), D (0.5%) and Y (0.5%) groups showed significantly reduced lesion score compare to control NE group.

Figure 5A:
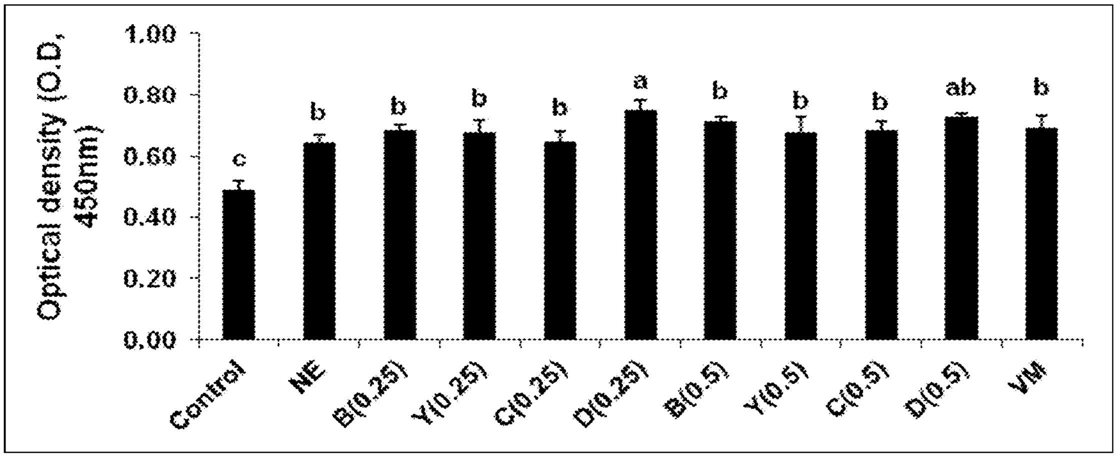
FIG. 5A depicts a serum antibody response against α-toxin antigen at 7 days post *C. perfringens* infection.

As shown in FIG. 5A, serum antibody levels against α-toxin (7 days post *C. perfringens* infection) were significantly higher in the D (0.25%) group compared with the infected NE control group. However, there was no significant difference in antibody levels between other diet groups and infected NE control group.

Figure 5B:
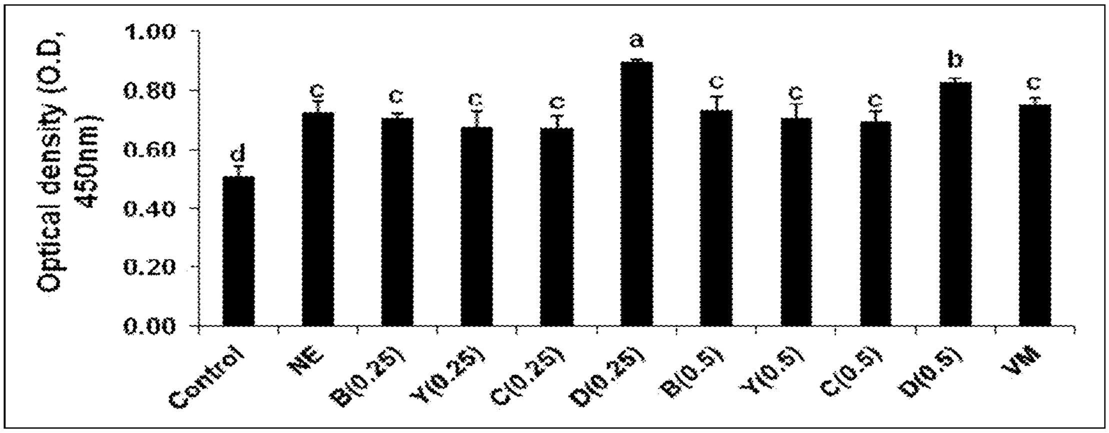
FIG. 5B depicts a serum antibody response against α-toxin antigen at 14 days post *C. perfringens* infection.

As shown in FIG. 5B, in birds fed the D (0.25%) and D (0.5%)-supplemented diet, serum antibody response against α-toxin (14 days post *C. perfringens* infection) showed notable increases compared with NE control group.

Figure 6A:
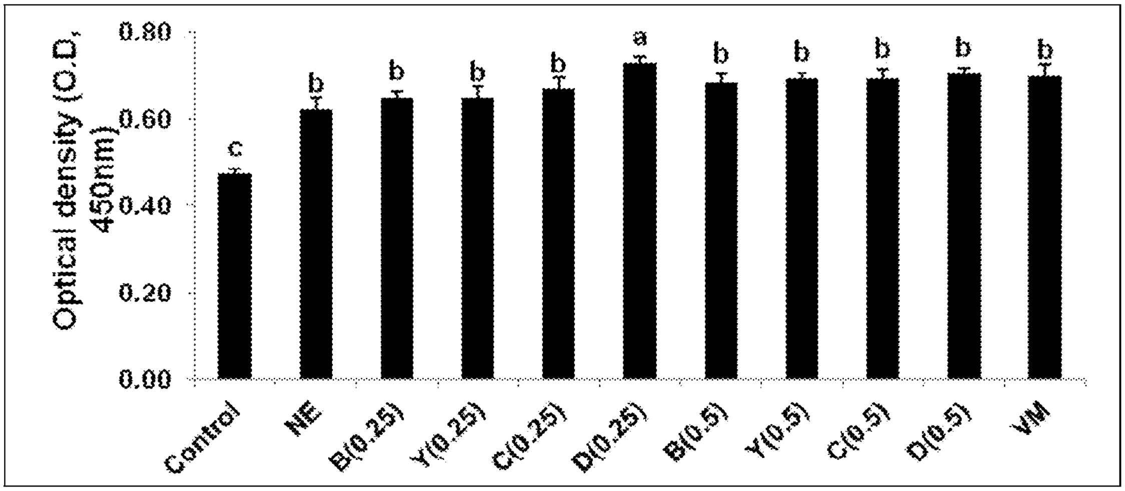
FIG. 6A depicts a serum antibody response against NetB toxin antigen at 7 days post *C. perfringens* infection.

As shown in FIG. 6A, in birds fed with D (0.25%), the serum antibody against NetB toxin (7 days post *C. perfringens* infection) showed increases compared with NE control group.

Figure 6B:
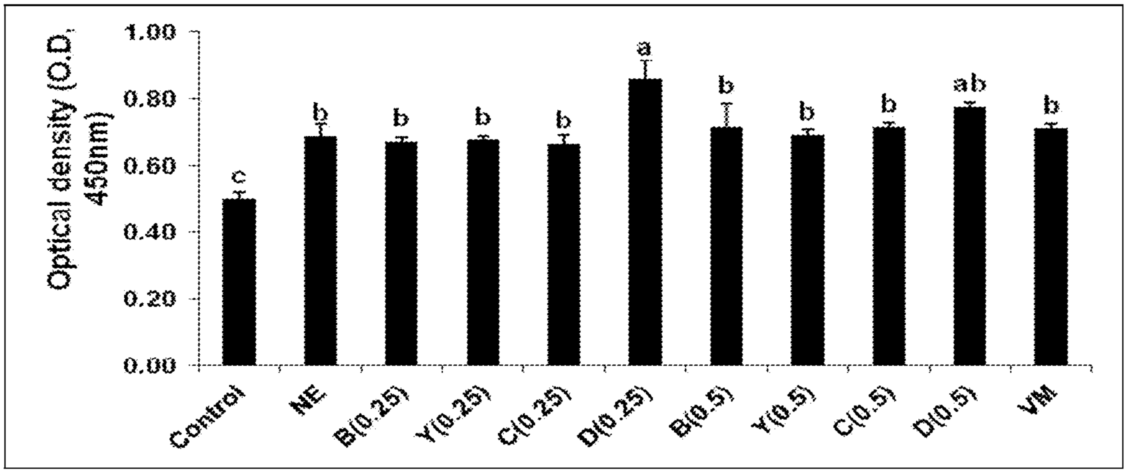
FIG. 6B depicts a serum antibody response against NetB toxin antigen at 14 days post *C. perfringens* infection.

As shown in FIG. 6B, in birds fed with D (0.25%), the serum antibody level against NetB toxin (14 days post *C. perfringens* infection) showed notable increases compared with NE control group.

Figure 7A:
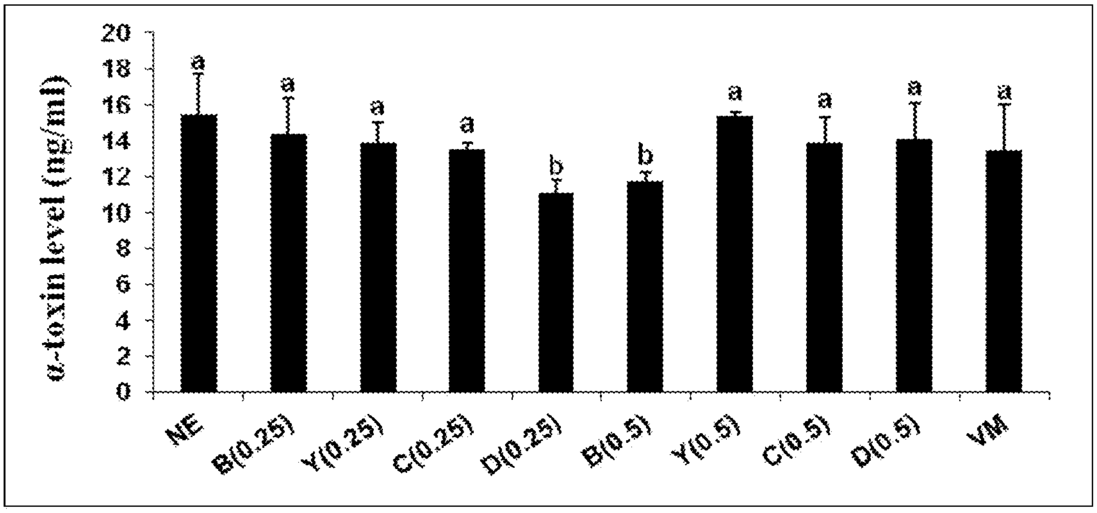
FIG. 7A depicts an effect of dietary supplementation with Amlan products on serum toxin. Sera were collected at 2 days post *C. perfringens* infection and used to measure the levels of α-toxin by ELISA.

As shown in FIG. 7A, serum α-toxin levels were significantly lower in the infected with D (0.25%) and B (0.5%) groups compared with the non-supplemented and infected NE controls.

Figure 7B:
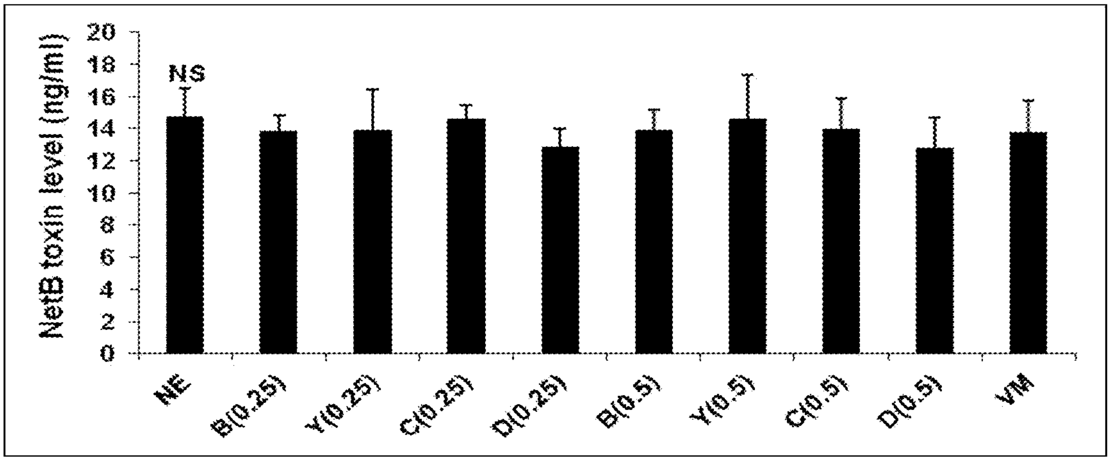
FIG. 7B depicts an effect of dietary supplementation with Amlan products on serum toxin. Sera were collected at 2 days post *C. perfringens* infection and used to measure the levels of NetB-toxin by ELISA.

As shown in FIG. 7B, serum NetB-toxin levels were lower in the infected with D (0.25%, 0.5%) and B (0.25%, 0.5%) groups compared with the non-supplemented and infected NE controls. However, there is no significant difference between groups.

To summarize this Example, chickens fed from hatch with a normal diet or with a diet supplemented with Amlan products (C, Y, B, D, and compared to the antibiotic VM), and immunity against NE was compared between the experimental and NE control groups. Chickens fed the D-supplemented diet and co-infected with *E. maxima* and *C. perfringens* showed significantly increased body weight gain, reduced lesion score, enhancement of the serum antibody levels to α-toxin or NetB toxin, and decreased serum α-toxin levels.

Example 6: Comparative Efficacy of Products to Virginiamycin Administered in the Feed for the Control of Necrotic Enteritis Caused by *Clostridium perfringens* in Broiler Chickens

TABLE 12

Summary

| Treatment | Feed Consumption D0-21 | Feed Consumption D14-21 | Feed Conversion D0-21 | Feed Conversion D14-21 | Weight Gain D0-21 | Weight Gain D14-21 | NE (0-3) Lesion Score |
|---|---|---|---|---|---|---|---|
| 1) Nonmed, noninfect | 5.480 a | 2.870 a | 1.773 c | 1.685 | 0.386 a | 0.212 a | 0.0 |
| 2) Nonmed, infect | 5.220 a | 2.714 ab | 2.183 a | 2.464 a | 0.307 b | 0.145 b | 0.5 a |
| 3) D infect | 4.959 ab | 2.590 abc | 2.086 ab | 2.199 ab | 0.305 b | 0.156 b | 0.3 abc |
| 4) D8, infect | 5.310 ab | 2.731 a | 2.091 ab | 2.331 a | .327 b | 0.153 b | 0.3 bcd |
| 5) DX, infect | 4.763 ab | 2.347 bc | 2.011 ab | 1.964 bc | 0.303 b | 0.152 b | 0.4 abc |

TABLE 12-continued

| Summary | | | | | | | |
|---|---|---|---|---|---|---|---|
| 6) D8X, infect | 5.191 ab | 2.553 abc | 2.185 a | 2.276 a | 0.319 b | 0.157 ab | 0.2 cd |
| 7) VM. 20 g/t, infect | 4.733 b | 2.312 c | 1.947 bc | 1.752 c | 0.316 b | 0.171 a | 0.5 ab |
| | Feed Consumption | | Feed Conversion | | Weight Gain | | % NE |
| Treatment | D0-28 | D14-28 | D0-28 | D14-28 | D0-28 | D14-28 | Mortality |
| 1) Nonmed, noninfect | 7.474 a | 4.863 a | 1.807 c | 1.781 c | 0.621 a | 0.447 a | 0.0 c |
| 2) Nonmed, infect | 7.022 ab | 4.516 ab | 2.254 a | 2.470 a | 0.465 c | 0.303 c | 10.9 a |
| 3) D infect | 6.561 ab | 4.192 bc | 1.984 bc | 1.994 bc | 0.482 bc | 0.333 bc | 6.3 ab |
| 4) D8, infect | 7.074 ab | 4.495 ab | 2.031 b | 2.131 b | 0.541 b | 0.367 b | 3.1 bc |
| 5) DX, infect | 6.410 b | 3.994 bc | 1.992 bc | 1.962 bc | 0.495 bc | 0.344 bc | 4.7 bc |
| 6) D8X, infect | 6.499 b | 3.861 c | 2.108 ab | 2.096 b | 0.489 bc | 0.327 bc | 4.7 bc |
| 7) VM. 20 g/t, infect | 6.313 b | 2.891 bc | 1.929 bc | 1.797 c | 0.512 b | 0.367 b | 1.6 bc |

The product key is:

| | |
|---|---|
| NE | Challenged birds no product fed |
| D | a blend of the clay, the yeast product, and monosodium glutamate, as in the previous study |
| D8 | A different formulation of the D product |
| DX | The formula of the D product using a different yeast product |
| D8X | The formula of the D8 product using a different yeast product |
| VM | 20 g/ton virginiamycin |
| NE | Challenged birds no product fed |

The study duration was 28 days and the target animal was a broiler chicken.

TABLE 13

| Treatments | | | | |
|---|---|---|---|---|
| Treatment | | Coccidial Challenge | *Clostridium perfringens* | Cages/Trt |
| T1 | Nonmedicated | DOT 14 | No | 8 |
| T2 | Nonmedicated | DOT 14 | DOT 19, 20, and 21 | 8 |
| T3 | D | DOT 14 | DOT 19, 20, and 21 | 8 |
| T4 | D8 | DOT 14 | DOT 19, 20, and 21 | 8 |
| T5 | DX | DOT 14 | DOT 19, 20, and 21 | 8 |
| T6 | D8X | DOT 14 | DOT 19, 20, and 21 | 8 |
| T7 | Virginamycin 20 g/t | DOT 14 | DOT 19, 20, and 21 | 8 |

Materials and Methods:

Experimental Ration: An unmedicated commercial type chicken starter ration compounded with feedstuffs commonly used in the United States was formulated. This ration (in mash form) was fed ad libitum from the date of chick arrival until Day 28 of the study. The diet formulation was included in the source data. Experimental treatment feeds were prepared from this basal starter feed. Quantities of all basal feed and test articles used to prepare treatment batches were documented. Treatment feeds were mixed to assure a uniform distribution of respective test article. The feed was distributed among cages of the same treatment.

Three samples were collected: one each from the beginning, middle, and end of the batch of treatment diet and mixed to form a composite sample. One composite sample was taken from the composite for each treatment.

Animals: One-day-old broiler male chicks were purchased from Cobb-Vantress hatchery, Cleveland, Ga. The strain was Cobb X Cobb. Breeder flock information was recorded. At the hatchery, the birds were sexed and received routine vaccinations. Only healthy appearing chicks were used in the study. Number and disposition of all birds not used for allocation were documented.

Housing: Upon arrival, chicks were raised in Petersime battery cages. At placement the birds were fed the treatment feeds. The floor space per animal was 0.63 sq.ft/bird. The feeder space per bird was 8 birds/43 cm×6.8 cm feeder. Thermostatically controlled gas furnace/air conditioner maintained uniform temperature. Even illumination was provided. The cage diagram was documented.

Bird Allocation and Cage Randomization: Cages were blocked by location in the battery with block size equal to treatments (7 cages per block). The study began when the birds were placed (day of hatch) (DOT 0) at which time they were allocated to the experimental cages. Only healthy birds were selected. On DOT 0, group body weights were recorded by cage. No birds were replaced during the course of the study.

Disease Induction: Feed and water were available ad libitum throughout the trial. On DOT 14, all birds were orally inoculated with a coccidial inoculum containing approximately 5,000 oocysts of *E. maxima* per bird. Coccidial oocyst inoculation procedures are described in SPR SOP. Starting on DOT 19, all birds, except Treatment 1, were given a broth culture of *C. perfringens* 108 cfu/ml. The birds were administered a fresh broth culture once daily for 3 days (on DOTs 19, 20, and 21).

DOT 0, 14, 21, and 28 Weights: All birds were weighed by cage on DOT 0, 14, 21 and 28. Feed was weighed in on DOT 0 and remaining feed was weighed on DOT 14, 21, and 28. The trial was terminated on DOT 28.

Necrotic Enteritis Intestinal Lesion Scoring: On DOT 21, three birds from each cage were selected, sacrificed, weighed, and examined for the degree of presence of Necrotic Enteritis lesions. The scoring was based on a 0 to 3 score, with 0 being normal and 3 being the most severe.

Management: The facility was checked thoroughly to assure that all cages had water and that feed was available in every cage. The building temperature's range was maintained at an appropriate temperature for the age of the birds. Even, continuous illumination was provided by fluorescent lamps hung vertically along the wall. Feed and water were given ad libitum.

In accordance with standard operating procedures (SOPs), the cages were checked twice daily. Observations included were the availability of feed and water, temperature control, and any unusual conditions. The birds were watched closely for any abnormal reactions.

When mortality birds were removed from cages, the cage number, date, weight of the bird, sex, and probable cause of death were recorded.

Data Analysis: Means for cage weight gain, feed consumption, feed conversion, lesion scores, and mortality were calculated.

Figure 8A:
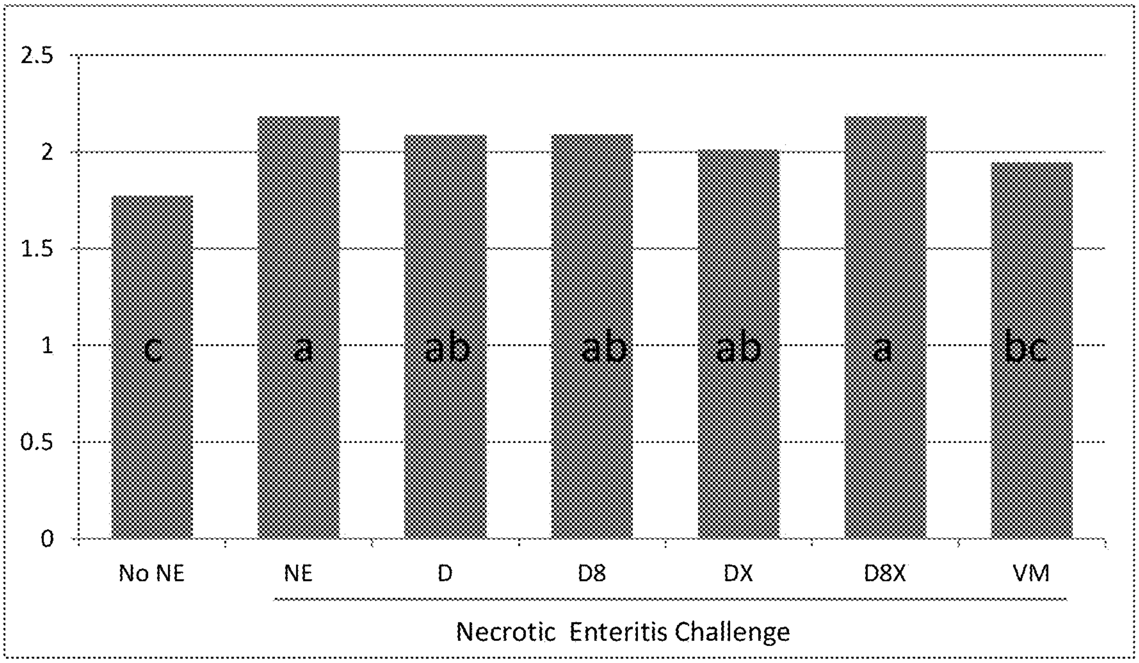
FIG. 8A depicts a comparison of feed conversion from Day 0-21 in an second in vivo experiment. In this experiment broiler chickens, except those on the non-challenged (No NE) were challenged to induce necrotic enteritis and fed no product (NE), a blend of the clay, the yeast product, and monosodium glutamate as in the previous experiment (D), a clay, yeast product, and monosodium glutamate with different inclusion rates (D8) and those two formulations using a different yeast product (DX and D8X), these products were compared to the antibiotic virginiamycin (VM). In this experiment on day 14 broilers were orally challenged with approximately 5,000 oocysts of *E. maxima* (a strain of coccidia) on days 19, 20, and 21 they were given a broth culture of *C perfringens* $10^8$ cfu/ml isolated from a clinical case of necrotic enteritis that produces both alpha and Net B toxins (except for the unchallenged control treatment (No NE)). The experiment lasted 28 days. In general, feed conversion for birds fed the different Amlan products was intermediate between those on the NE or VM treatments from day 0 to 21. However, birds fed product D8X did not follow this pattern having feed conversion that was as poor, statistically and numerically, as those on the NE treatment for this time period.

FIG. 8A depicts feed conversion from Day 0-21. In general, feed conversion for birds fed the different treatments was intermediate between those on the NE (birds challenged to induce necrotic enteritis but fed no product) or VM (birds challenged to induce necrotic enteritis and fed virginiamycin) treatments from day 0 to 21. However, birds fed product D8X did not follow this pattern having feed conversion that was as poor, statistically and numerically, as those on the NE treatment with no product for this time period.

Figure 8B:
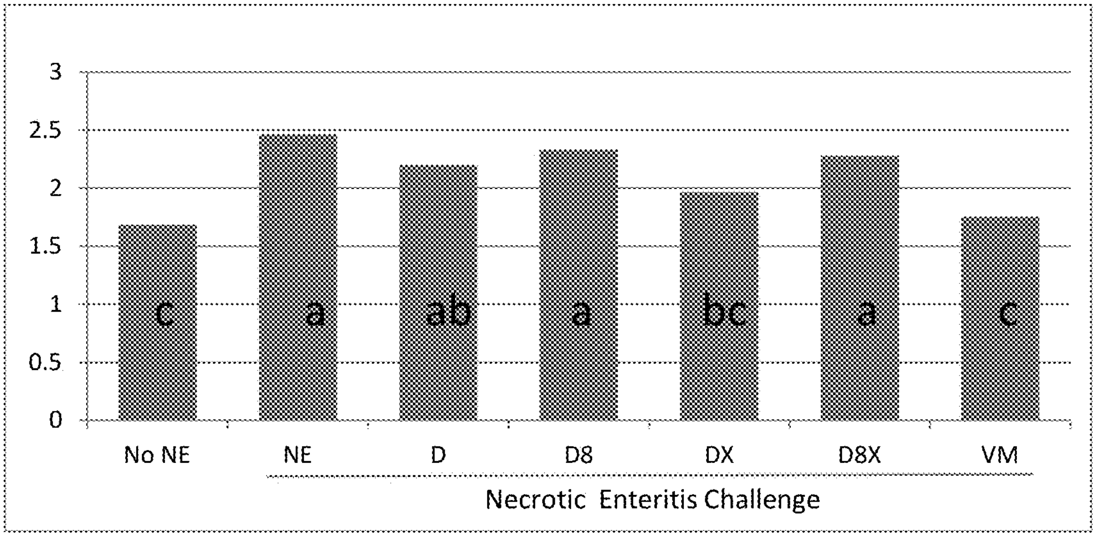
FIG. 8B depicts feed conversion from Day 14-21. Feed conversion for challenged birds fed Treatment DX was significantly better than birds on the NE treatment (challenged but fed no product) for the day 14-21 time period and was statistically equal to the diet with VM added.

FIG. 8B depicts feed conversion from Day 14-21. Feed conversion for challenged birds fed Treatment DX was significantly better than birds on the NE treatment (challenged but fed no product) for the day 14-21 time period and was statistically equal to the diet with VM added.

Figure 8C:
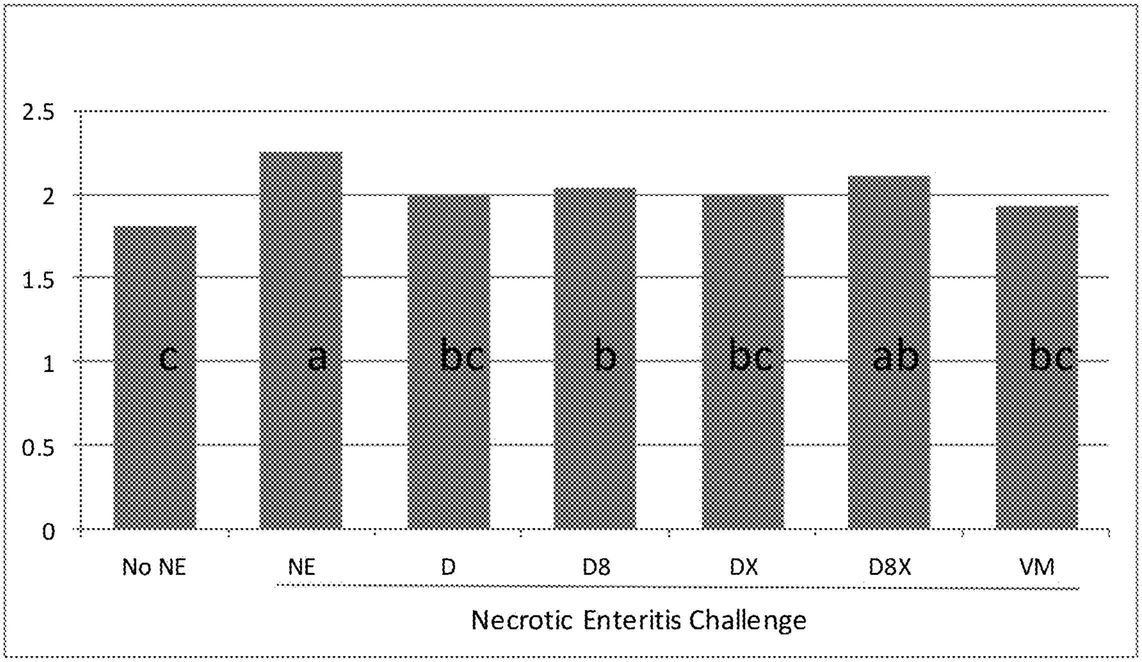
FIG. 8C depicts feed conversion from Day 0-28. All products except D8X were significantly better than NE with no product. The products D and DX were the best of the tested products, similar to the birds on the VM treatment, and not statistically different than the birds given no NE challenge.

FIG. 8C depicts feed conversion from Day 0-28. All products except D8X were significantly better than NE with no product. The products D and DX were the best of the tested products, similar to the birds on the VM treatment, and not statistically different from the birds given no NE challenge.

Figure 9A:
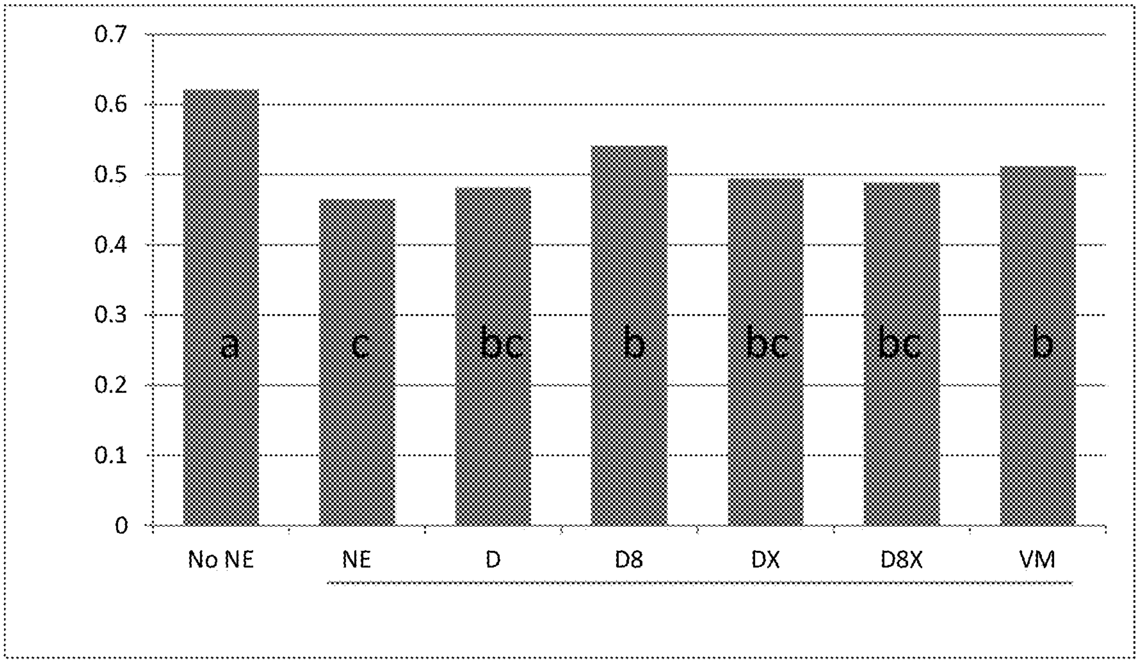
FIG. 9A depicts weight gain from Day 0-28. Gain was improved by VM compared to the NE control without any product. D8 was statistically equal and numerically better when compared to VM. All other products were intermediate between NE with no product and VM.

FIG. 9A depicts weight gain from Day 0-28. Gain was improved by VM compared to the NE control without any product. D8 was statistically equal and numerically better when compared to VM. All other products were intermediate between NE with no product and VM.

Figure 9B:
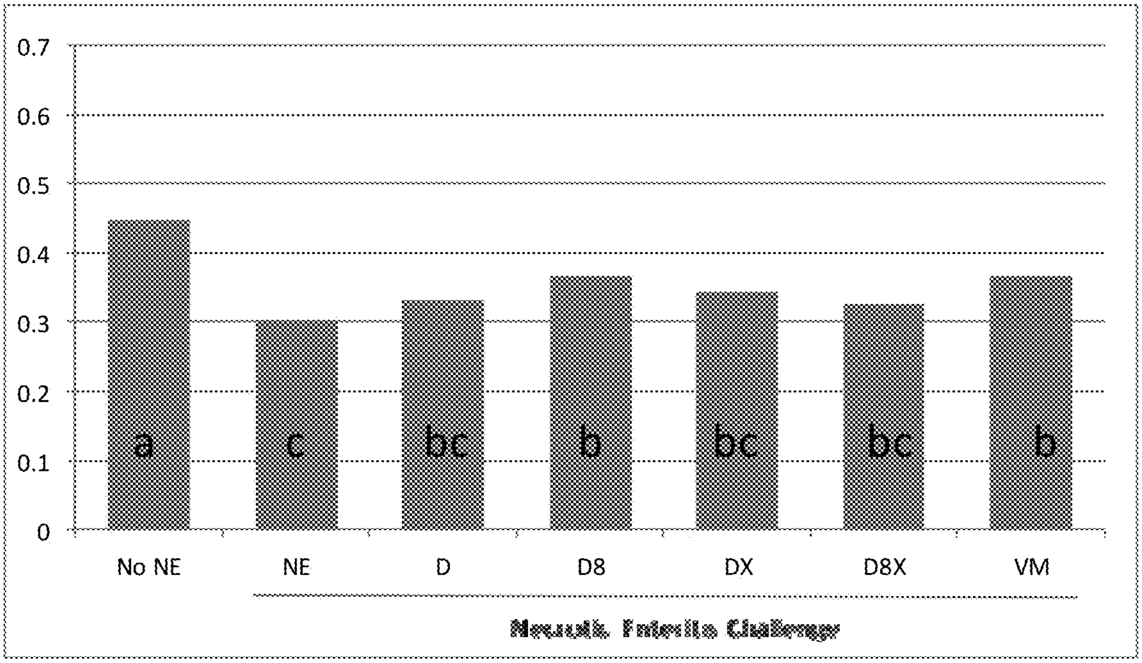
FIG. 9B depicts weight gain from Day 14-28. Gain followed similar patterns for day 14-28 as for day 0-28, except that D8 was numerically equal to VM.

FIG. 9B depicts weight gain from Day 14-28. Gain followed similar patterns for day 14-28 as they did for day 0-28, except that D8 was numerically equal to VM.

Figure 10:
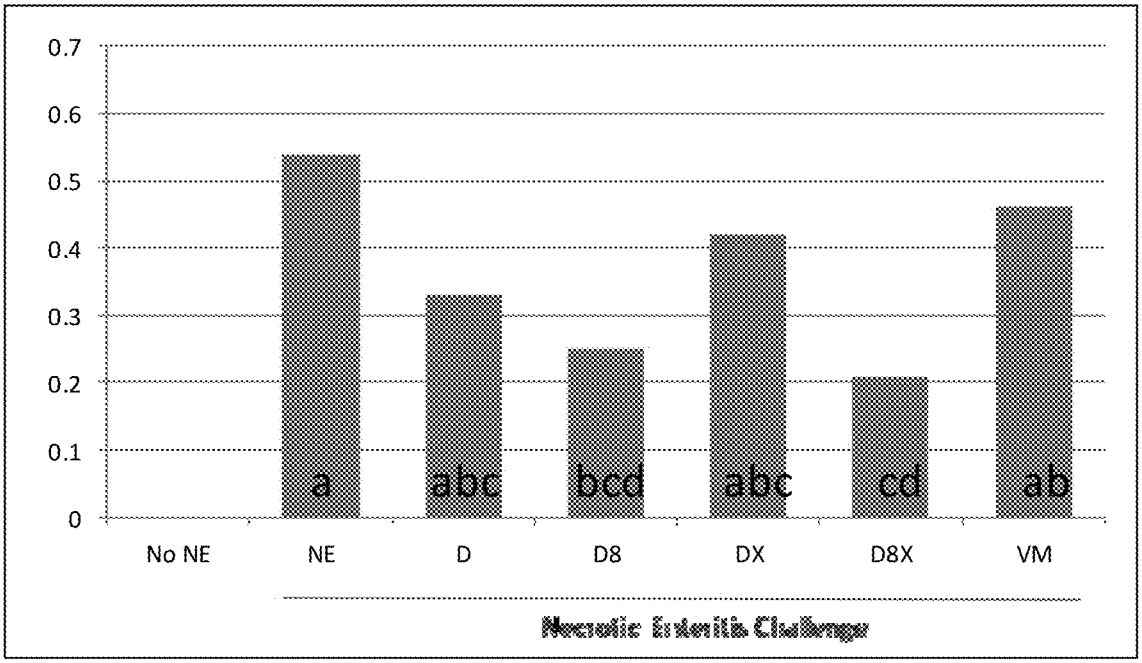
FIG. 10 depicts lesion scores. Lesion scores for birds fed D8 and D8X were lower than for birds fed VM and may not have been statistically different than those birds not challenged with NE.

FIG. 10 depicts lesion scores. Lesion scores for birds fed D8 and D8X were lower than for birds fed VM and may not have been statistically different than those birds not challenged with NE.

Figure 11:
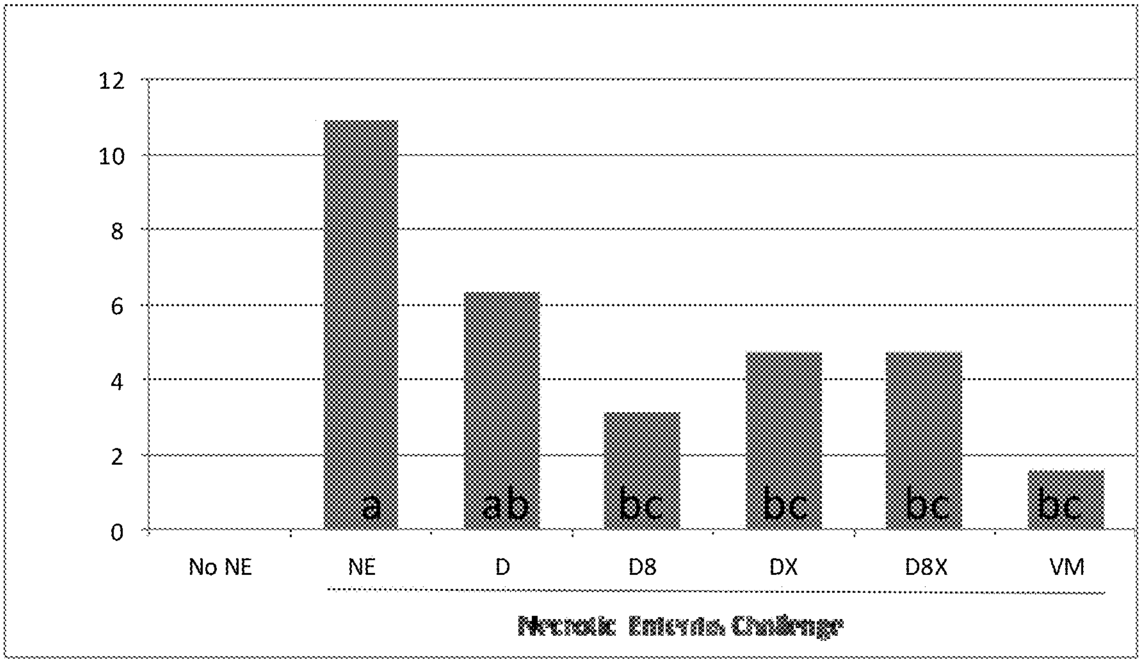
FIG. 11 depicts NE mortality. All products except for D decreased Mortality compared to NE challenged birds with no product and were equal to those fed VM.

FIG. 11 depicts NE mortality. All products except for D decreased Mortality compared to NE challenged birds with no product and were statistically equal to those fed VM.

Example 7: Effects of Products Against the Effects of Necrotic Enteritis in Broiler Birds The purpose of this Example was to evaluate different formulas and dosages of the previously discovered products on Necrotic Enteritis (NE) clinical signs, immunopathology and cytokine responses in broiler chickens co-infected with *Eimeria maxima* and *Clostridium perfringens* in a Necrotic Enteritis (NE) Disease Model. The NE disease model used for this trial (Park S S, Lillehoj H S, et al. Immunopathology and cytokine responses in broiler chickens coinfected with *Eimeria maxima* and *Clostridium perfringens* with the use of an animal model of necrotic enteritis. Avian Diseases 2008; 52:14-22; Jang S I, Lillehoj H S, et al. Vaccination with *Clostridium perfringens* recombinant proteins in combination with Montanide™ ISA 71 VG adjuvant increase protection against experimental necrotic enteritis in commercial broiler chickens. Vaccine 2012; 30:5401-5406).

Materials and Methods.

The products were a blend of clay, a yeast product, and monosodium glutamate in a formula previously found to be effective (D), in the current experiment it was included at four different inclusion rates (0.35, 0.25, 0.15 and 0.05%), also included were products containing the same ingredients as the previous product but with four different formulations of ingredients in the formula of the Product (designated DS, DSF, D8, and D8F5). The antibiotic virginiamycin (VM) was also included as a treatment. The chickens were one-day-old broiler birds (Ross/Ross) hatched at the Longeneckers Hatchery (Elizabethtown, Pa.) transported by mail truck and housed in starter brooder units. The birds were kept in brooder pens in an *Eimeria*-free facility and transferred into large hanging cages in a separate location where they were infected and kept until the end of experimental period for the live challenge infection study. All procedures regarding transportation, measuring body weight, infection, and collecting blood and spleen were in accordance with established guidelines for animal experiments.

All birds were fed a non-medicated commercial basal ration of 17% crude protein from 1-18 days of age. The feed was mixed with the D at different inclusion rates (0.35, 0.25, 0.15, and 0.05% of the diet) or different formulations of the product (DS, DSF, D8, D8F) included at 0.25% of the diet. The antibiotic VM (22 ppm) was also included as a treatment. At 18 days, the feed was replaced with commercial non-medicated feed containing 24% crude protein starter feed with treatment products added as in the 17% CP ration.

Strains of *Eimeria* spp. were maintained and propagated in accordance with established procedure. *E. maxima* (41A) were cleaned by floatation on 5% sodium hypochlorite, washed three times with PBS, and viability was enumerated by trypan blue using a hemocytometer. The oocyst number is based on only sporulated oocysts. At day 14, chickens were inoculated esophageally with 10,000 of *E. maxima* using an inoculation needle.

Four days after *Eimeria* infection, birds of NE Groups were inoculated esophageally with $1\times10^9$ CFU *Clostridium perfringens* each using an inoculation needle.

Birds were weighed just before challenge with *E. maxima* (EM), 0, and 2nd days post *C. perfringens* challenge to calculate the weight gain.

To determine a lesion score, birds (5 birds/group) were sacrificed at 2 day post *C. perfringens* (CP) infection. Approximately 20 cm intestinal segments extending 10 cm anterior and posterior to diverticulum obtained and cut longitudinally. Lesion scores were evaluated by 3 independent observers from 0 to 4 in ascending order of severity of the lesion.

On each of 0, 2, 7 and 14 days post CP infection, a total of 12 birds (5/group) were sampled for serum for antibody titers (collect individually). For sera, blood samples were obtained from individual birds (3 ml/bird), allowed to clot overnight at 4° C., and the sera were collected.

Serum samples were tested for antibodies against *clostridium* using an established ELISA. Briefly, microtiter plates were coated overnight with 200 ng/well of the recombinant *clostridium* antigen, washed with PBS-0.05% Tween, and blocked with PBS-1% BSA. Serum dilutions added, incubated with continuous gentle shaking, washed, and bound Ab detected with peroxidase-conjugated rabbit anti-chicken IgG (Sigma) and peroxidase-specific substrate. Optical density (OD) was determined at 450 nm using a microplate reader (Bio-Rad, Richmond, Calif.).

Serum samples were tested for antigens against α-toxin or NetB using an established ELISA. Briefly, microtiter plates were coated overnight with 0.5 μg/well of the mAb to α-toxin or NetB toxin, washed with PBS-0.05% Tween, and blocked with PBS-1% BSA. Chicken serum dilutions added, incubated with continuous gentle shaking, washed, and bound Ab detected with peroxidase-conjugated rabbit anti-α-toxin or NetB toxin and peroxidase-specific substrate. Optical density (OD) was determined at 450 nm using a microplate reader (Bio-Rad, Richmond, Calif.).

For statistical analysis, all values were expressed as mean±SEM. Mean values for body weight gain and lesion score were compared among groups by the Duncan's Multiple Range test following ANOVA using SPSS 15.0 for Windows (SPSS Inc., Chicago, Ill.). Differences among means were considered significant at $p<0.05$.

TABLE 14

Experimental Design

| Group # | Bird (Number) | Product | Inclusion, % | Infection for NE (EM + CP)* |
|---|---|---|---|---|
| 1 | 20 | No | — | – |
| 2 | 20 | No | — | + |
| 3 | 20 | D | 0.35 | + |
| 4 | 20 | D | 0.25 | + |
| 5 | 20 | D | 0.15 | + |
| 6 | 20 | D | 0.05 | + |
| 7 | 20 | DS | 0.25 | + |
| 8 | 20 | DSF | 0.25 | + |
| 9 | 20 | D8 | 0.25 | + |
| 10 | 20 | D8F | 0.25 | + |
| 11 | 20 | VM | 22 ppm | + |

*Chickens were orally infected with $1.0 \times 10^4$ oocysts/bird of *E. maxima* (EM) at day 15 post-hatch and with $1.0 \times 10^9$ CFU/bird of *C. perfringens* (CP) at day 19 post hatch (experimental day 14 and 18, respectively).

220 broiler birds (20/group) were used and housed in Petersime brooder pens. The finisher unit was an 80 hanging cage unit where the birds were transferred at day 18.

Chickens arrived on day 0 and moved to Petersime units the same day. The chickens were moved to large cages on day 18. Birds were infected with 10,000 sporulated oocysts of *E. maxima* at day 14 and infected with $1\times10^9$ CFU of *C. perfringens* on day 18. Blood was collected on day 14, 18, 20, 25 and 32. Lesions were scored on day 20. Body weight was determined on day 14, 20 and 25 (see, e.g., FIG. 1).

Figure 12A:
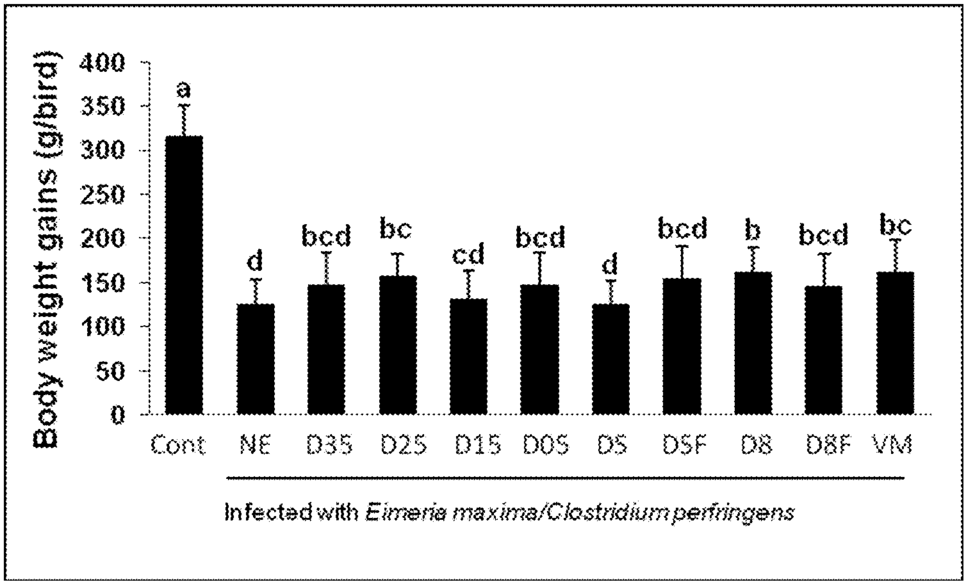
FIG. 12A depicts a comparison of the body weight gains in broiler chickens in a third in vivo study determined from day of *Eimeria maxima* infection to 2 days post *C. perfringens* infection. Birds were infected with 10,000 sporulated oocysts of *E. maxima* at day 14 post hatch. After 4 days *Eimeria maxima* infection, birds were inoculated with $1\times10^9$ CFU *C. perfringens*. In this experiment there is a non-challenged control (Cont) a group challenged to induce necrotic enteritis but fed no product (NE), the product D formulation at 0.35, 0.25, 0.15, and 0.05% inclusion (D35, D25, D15, and D05) also included are products that combine the ingredients at different rates (DS, DSF, D8 D8F), and the final group received 20 g/ton of virginiamycin in the diet (VM).
Figure 12B:
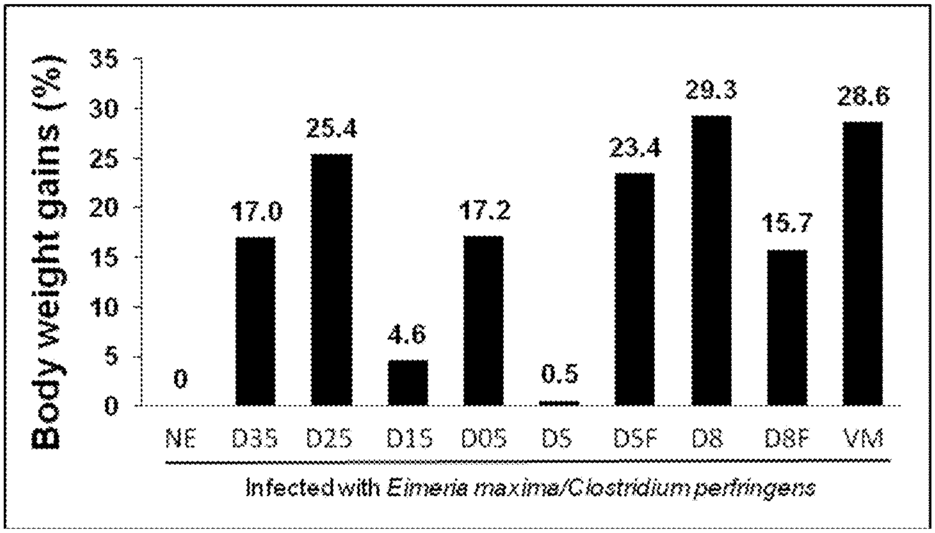
FIG. 12B depicts a comparison of the percentage increase in body weight gains relative to the birds on the necrotic enteritis challenge control with no product. NE is the group challenged to induce necrotic enteritis but fed no product; VM is the group that received 20 g/ton of virginiamycin in the diet).

As shown in FIGS. 12A-B, chickens fed with diets containing 0.25% of product D, or 0.25% of D8 showed increased body weight gains from the day of the *Eimeria* challenge to 2 days post CP infection, of 25.4% or 29.3%, respectively, compared with the infected birds given the non-supplemented diet (NE control group).

Figure 13A:
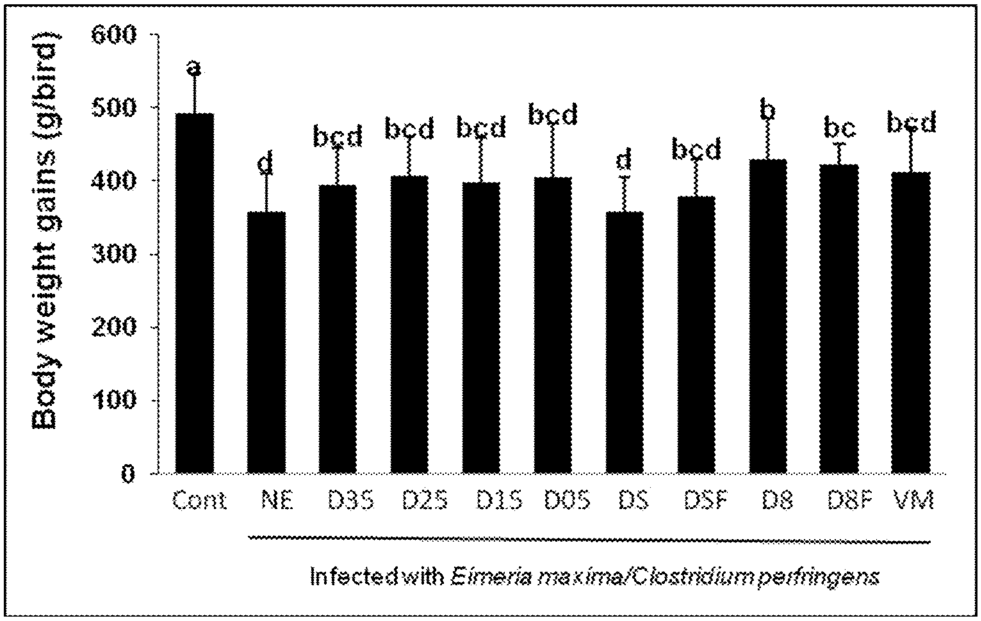
FIG. 13A depicts a comparison of the body weight gains in broiler chickens. Body weights gains were determined starting the day of *C. perfringens* infection and ending at 7 days post *C. perfringens* infection.
Figure 13B:
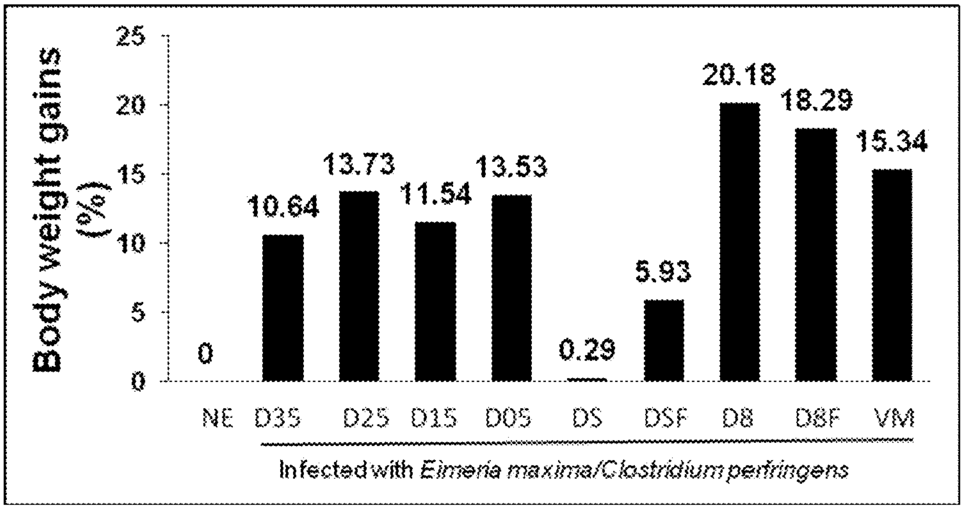
FIG. 13B depicts a comparison of the percentage increase in body weight gains relative to the necrotic enteritis challenge control with no product.

As shown in FIGS. 13A-B, chickens fed the 0.25% of D8 or D8F supplemented diet showed 20.18% and 18.29% increase in body weight gains, respectively, compared with the infected birds given the non-supplemented diet (NE control group).

Figure 14:
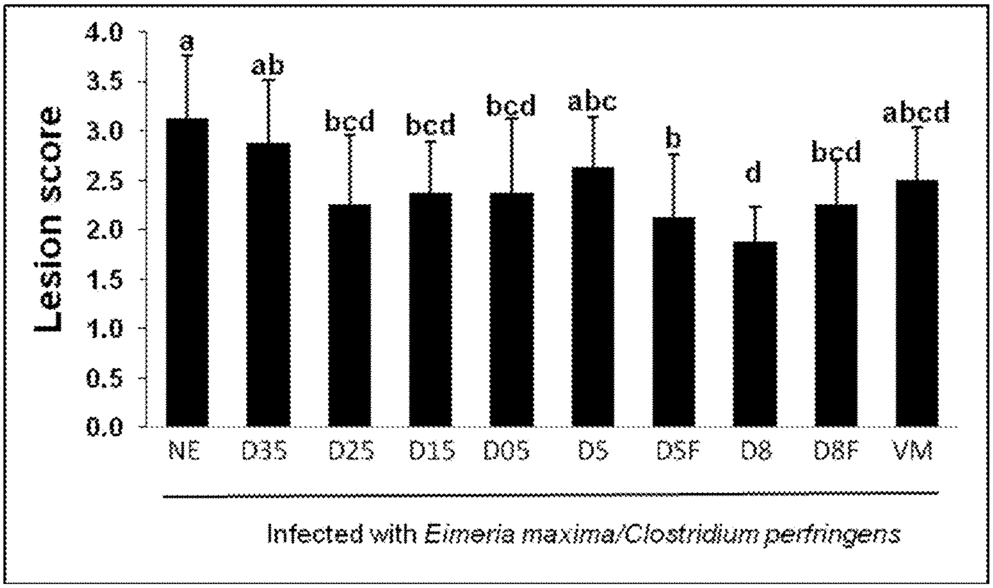
FIG. 14 depicts an effect of Products on intestinal lesion scores, scores are an average of 5 birds per group examined on d 2 post *C. perfringens* infection.

As shown in FIG. 14, birds fed with D at the 0.25, 0.15, or 0.05% inclusion levels, or DSF, D8, and D8F groups showed significantly reduced lesion score compared with the infected birds given the non-supplemented diet.

Figure 15A:
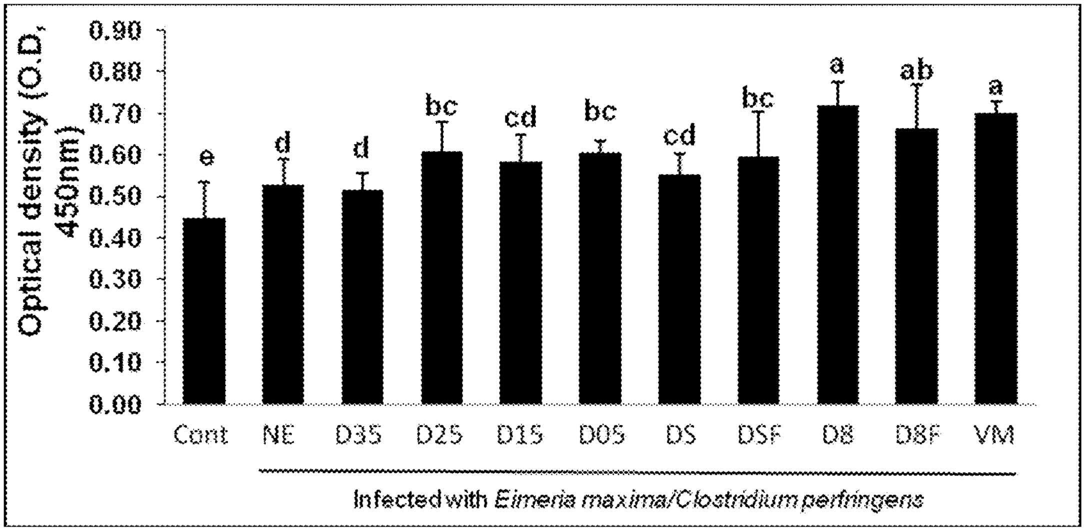
FIG. 15A depicts a serum antibody response against α-toxin antigen at 2 days post *C. perfringens* infection.

As shown in FIG. 15A serum antibody levels against α-toxin were significantly higher in birds fed D at the 0.05 or 0.25% inclusion rate or DSF, D8, or D8F at the 0.25% inclusion rate or the VM groups compared with the infected birds given the non-supplemented diet (NE control group) on d 2 post *C. perfringens* infection.

Figure 15B:
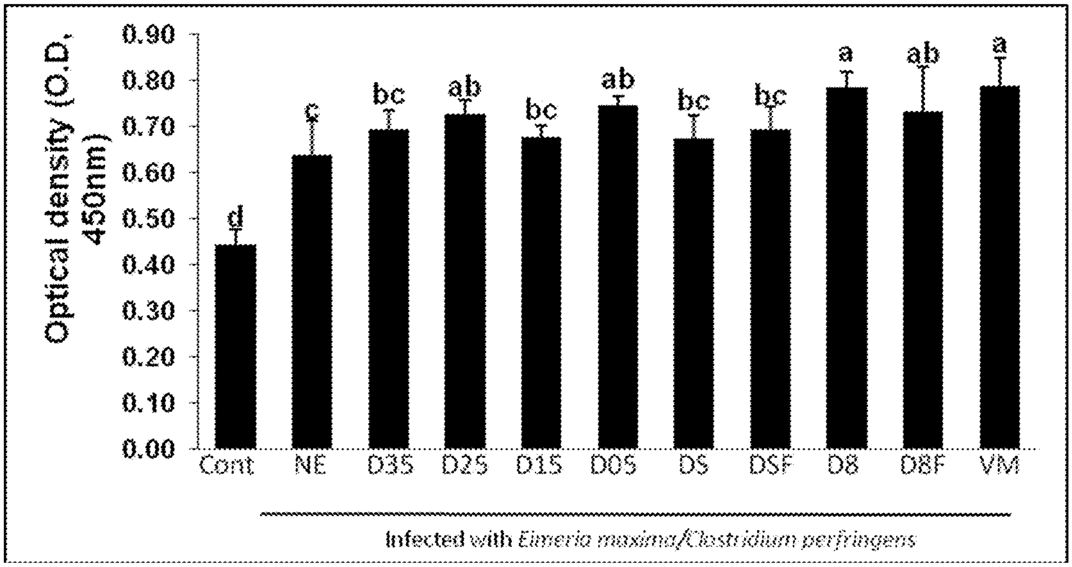
FIG. 15B depicts a serum antibody response against α-toxin antigen at 7 days post *C. perfringens* infection.

As shown in FIG. 15B on d 7 post *C perfringens* infection In birds fed the D formula at 0.25 or 0.05% inclusion or the D8 or D8F at 0.25% inclusion or the VM-supplemented diet, optical density showed notable increases in antibodies to α-toxin compared with the NE control group.

Figure 16A:
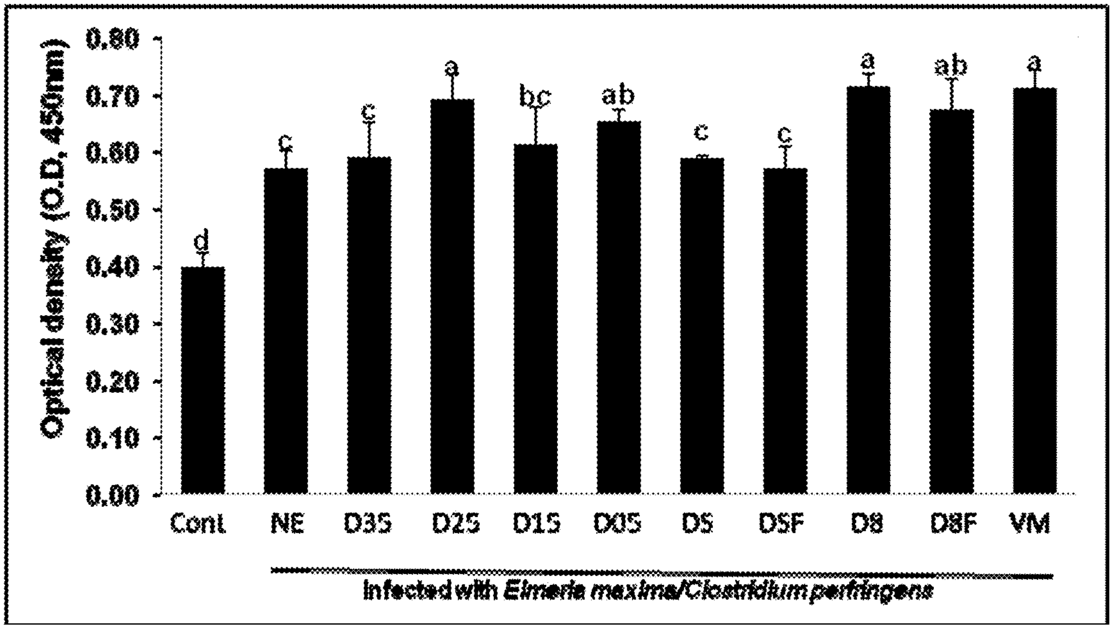
FIG. 16A depicts a serum antibody response against NetB toxin antigen at 2 days post *C. perfringens* infection.

As shown in FIG. 16A, serum antibody levels against the NetB toxin antigen were higher at day 2 post *C. perfringens* infection in birds that were fed product D at 0.05 or 0.25% inclusion rate or D8 or D8F at the 0.25% inclusion, or VM, as the optical density showed increases compared with the NE control group.

Figure 16B:
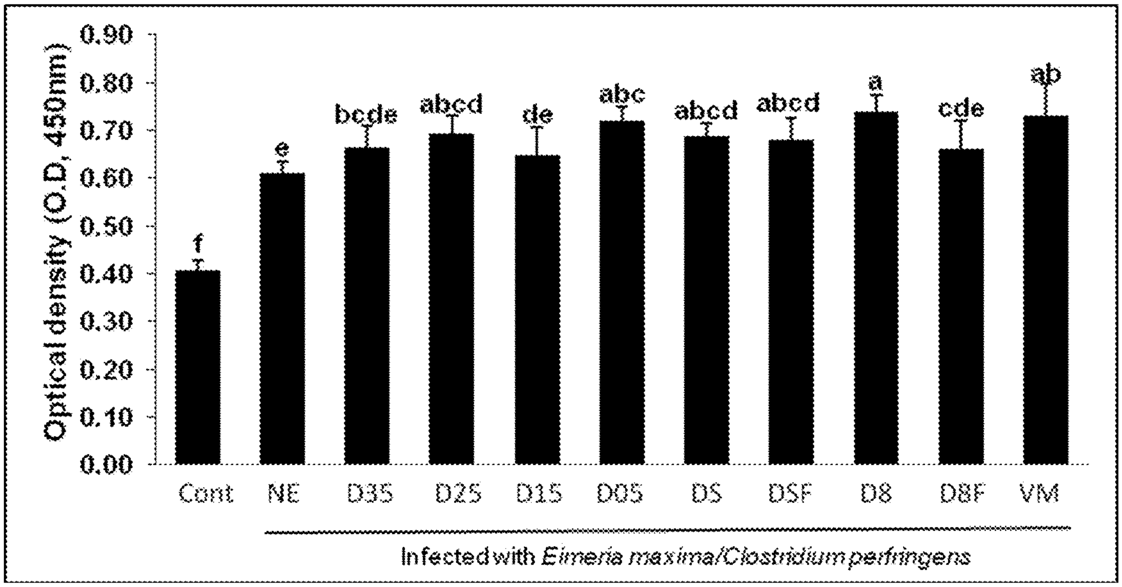
FIG. 16B depicts a serum antibody response against NetB toxin antigen at 7 days post *C. perfringens* infection.

As shown in FIG. 16B, birds fed the D formula at 0.05 and 0.25% inclusion rate or DS, DSF, D8, and VM all showed increased serum antibody response against NetB toxin antigen at 7 days post *C. perfringens* infection.

Figure 17A:
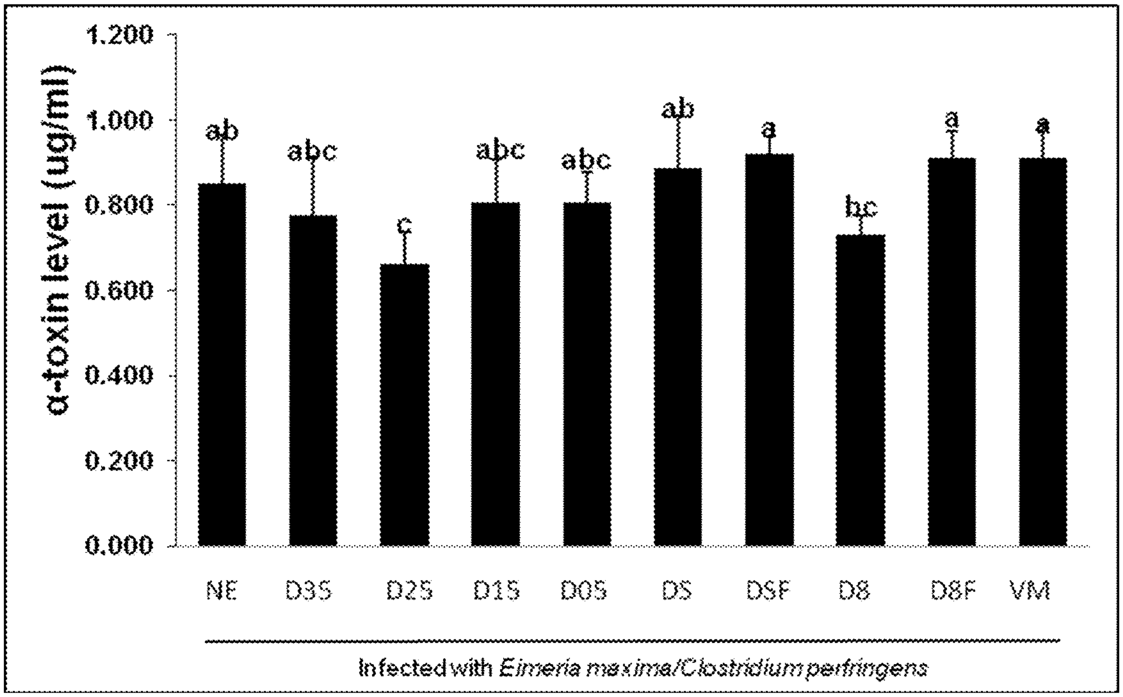
FIG. 17A depicts an effect of dietary supplementation on serum α-toxin levels. Sera were collected at d-2 post *C. perfringens* infection and used to measure the levels of α-toxin by enzyme-linked immunosorbent assay (ELISA).

As shown in FIG. 17A, serum α-toxin levels at day 2 post *C. Perfringens* infection were significantly lower in the infected birds fed with D (0.25%) compared with the non-supplemented, NE infected controls. The level of serum alpha toxin indicates severity of *Clostridium* infection. This result may indicate reduction of *C. perfringens* alpha toxin level by the product via direct or indirect action.

Figure 17B:
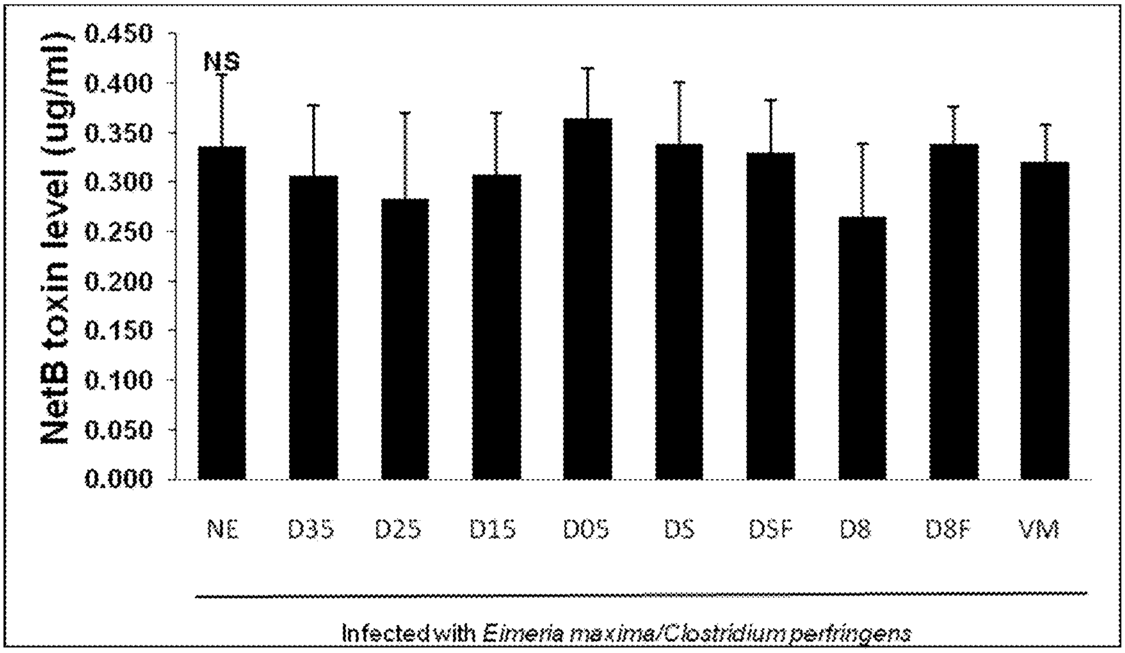
FIG. 17B depicts an effect of dietary supplementation on serum NetB-toxin levels. Sera were collected at d-2 post *C. perfringens* infection and used to measure the levels of NetB-toxin by ELISA.

As shown in FIG. 17B, serum NetB-toxin levels at d 2 post *C. perfringens* infection were substantially lower (although not statistically significant) in the NE infected birds fed D (0.25%) and D8 (0.25%) compared with the non-supplemented and infected NE controls. The level of NetB toxin indicates severity of *Clostridium* infection. This result may indicate reduction of *C. perfringens* NetB toxin level by the product via direct or indirect action.

As shown in FIGS. 18A-B, intraepithelial lymphocytes IL8 expression decreased in the groups supplemented with all products D, DS, DSF, D8 or VM compared with NE control birds. Intraepithelial lymphocytes (LITAF) expression decreased in the group supplemented with product D at the 0.35, 0.25, or 0.15% inclusion levels, or products DSF, D8, D8F or the antibiotic VM. Adding DS at 0.25% of the diet showed decreased LITAF level.

As shown in FIGS. 18C-D, IL-6 and iNOS expression generally decreased in the groups supplemented with all products D, DS, DSF, D8 or the antibiotic VM compared with NE control birds. In general, these results indicate beneficial effects of feeding young broiler chickens with these products.

As shown in FIGS. 19A-C, in the spleen IL8 expression increased in the groups supplemented with D8F. While LITAF expression decreased in the group supplemented with Amlan product D8 (0.25%) and D8F. However, DSF group showed increased LITAF level. TNFSF15 expression decreased in the group supplemented with Amlan product D at all inclusion levels or the D8 or D8F products, or the antibiotic VM.

As shown in FIGS. 19D-F, in the spleen there was no significant difference between groups in IL-6 cytokine expression. While iNOS expression decreased in the groups supplemented with product D at the 0.25% or 0.05% inclusion rates, or the product D8F, or the antibiotic VM. Additionally, IL-1β expression decreased in the group supplemented with product D at the 0.35 or 0.15% inclusions, or the product DS, or D8.

To summarize this Example, chickens were fed from hatch with a normal diet or a diet that had additions of the products D, DS, DSF, D8, D8F, or VM, and immunity against NE was compared among the experimental and NE control groups. Chickens fed the 0.25% of D, or 0.25% of D8 supplemented diet and co-infected *E. maxima* and *C. perfringens* showed significantly increased body weight gain, reduced gut lesion scores, enhancement of the serum antibody levels to α-toxin or NetB toxin, and decreased serum α-toxin levels. The gene transcript levels for IL-6, IL8, iNOS, and TNFSF15 in the intestine were reduced in the group supplemented with 0.25% of product D, DS, DSF, D8, and D8F, respectively. When 0.25% of product D was added to the diet birds showed a decreased level on cytokine expression such as TNFSF15, and iNOS in spleen. These results indicate the beneficial effects of the addition of 0.25% of product D, or 0.25% supplementation of D8 on mitigating the harmful effects of NE disease in broiler chickens.

FIG. 12A depicts a comparison of the body weight gains in broiler chickens determined from day of *Eimeria maxima* infection to 2 days post *C. perfringens* infection. Birds were infected with 10,000 sporulated oocysts of *E. maxima* at day 14 post hatch. After 4 days *Eimeria maxima* infection, birds were inoculated with $1\times10^9$ CFU C.PCP. (Cont is non-challenged control group; NE is the group challenged to induce necrotic enteritis but fed no product; VM is the group that received 20 g/ton of virginiamycin in the diet)

FIG. 12B depicts a comparison of the percentage increase in body weight gains relative to the birds on the necrotic enteritis challenge control with no product based on 1.

FIG. 13A depicts a comparison of the body weight gains in broiler chickens Body weights gains were determined starting the day of *C. perfringens* infection and ending at 7 days post *C. perfringens* infection.

FIG. 13B depicts a comparison of the percentage increase in body weight gains relative to the necrotic enterits challenge control with no product based on FIG. 3-1

FIG. 14 depicts an effect of Products on intestinal lesion scores, scores are an average of 5 birds per group examined on d 2 post *C. perfringens* infection FIG. 15A depicts a serum antibody response against α-toxin antigen at 2 days post *C. perfringens* infection.

FIG. 15B depicts a serum antibody response against α-toxin antigen at 7 days post *C. perfringens* infection.

FIG. 16A depicts a serum antibody response against NetB toxin antigen at 2 days post *C. perfringens* infection.

FIG. 16B depicts a serum antibody response against NetB toxin antigen at 7 days post *C. perfringens* infection.

FIG. 17A depicts an effect of dietary supplementation on serum α-toxin levels. Sera were collected at d-2 post *C. perfringens* infection and used to measure the levels of α-toxin by ELISA.

FIG. 17B depicts an effect of dietary supplementation on serum NetB-toxin levels. Sera were collected at d-2 post *C. perfringens* infection and used to measure the levels of NetB-toxin by ELISA.

FIGS. 18A-B depict cytokine production in the jejunum intraepithelial lymphocytes at 2 days post *C. perfringens* infection.

FIG. 18C-D depict cytokine production in the jejunum intraepithelial lymphocytes of birds at 2 days post *C. perfringens* infection.

FIGS. 19A-C depict cytokine production in the spleen of birds at 2 days post *C. perfringens* infection.

FIGS. 19D-F depict cytokine production in the spleen of birds at 2 days post *C. perfringens* infection.

The invention is further described by the following numbered paragraphs:

1. A method for treating an enteric disease in an animal in need thereof comprising administering a mixture comprising a clay, a yeast product and a glutamate to the animal, thereby treating the enteric disease.

2. The method of paragraph 1 wherein the enteric disease is caused by a *Clostridium* bacteria or an Eimeriaprotazoa.

3. The method of paragraph 1 or 2, wherein the enteric disease is necrotic enteritis, coccidiosis, *Clostridia difficile* infection, chronic or hemorrhagic bowel disease, enterotoxemia, shigalosis, diarrhea or a disease caused by bacterial or food or water born endotoxins and/or exotoxins.

4. The method of any one of paragraphs 1 to 3, wherein the animal is a poultry species, a dog, a cat, a pig, a cattle, a sheep, a goat, a horse or a human.

5. The method of any one of paragraphs 1 to 3, wherein the animal is an aquatic species.

6. The method of paragraph 5, wherein the aquatic species is a shrimp or a farmed fish.

7. The method of any one of paragraphs 1 to 6, wherein the mixture is administered as a diet supplement.

8. The method of any one of paragraphs 1 to 7, wherein the mixture is about 50 to 90% (w/w) of the clay, about 10 to 50% (w/w) of the yeast product and about 0.01 to 15% (w/w) of the glutamate.

9. The method of any one of paragraphs 1 to 8, wherein the clay is a calcium montmorillonite clay.

10. The method of any one of paragraphs 1 to 8, wherein the clay is a sorbent mineral, a diatomaceous earth, a silicate, a zeolite, an attapulgite, or a combination thereof.

11. The method of any one of paragraphs 1 to 10, wherein the clay is heated to between about 100° C. to about 800° C.

12. The method of any one of paragraphs 1 to 11, wherein the clay is ground to a particle size of about 20 to 50 microns.

13. The method of any one of paragraphs 1 to 12, wherein the yeast product is a *Pichia guilliermondii* yeast product.

14. The method of paragraph 13, wherein the yeast product is a citric acid press cake.

15. The method of any one of paragraphs 1 to 12, wherein the yeast product is a yeast fermentation product.

16. The method of any one of paragraphs 1 to 15, wherein the yeast product is a yeast component.

17. The method of paragraph 16, wherein the yeast component is a yeast mannan, a yeast cell wall, a mannan oligosaccharide, a beta glucan, a fiber, a carbohydrate source, a prebiotic, or a combination thereof.

18. The method of any one of paragraphs 1 to 17, wherein the yeast product is a yeast fermentation product.

19. The method of any one of paragraphs 1 to 18, wherein the glutamate is monosodium glutamate.

20. The method of any one of paragraphs 1 to 18, wherein the glutamate is a glutamic acid, α-ketoglutarate, glutamine, L-glutamic acid or L-glutamine or a derivative thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for treating an enteric disease comprising a bacterial enteric disease comprising Necrotic Enteritis (NE) or mitigating the effects of exposure to a bacterial enteric disease causing organism comprising a *Clostridium* in an avian or pig susceptible to the enteric disease comprising administering to the avian or pig a composition comprising a mixture of 50 to 80% (w/w) of a *Clostridium*-toxin adsorbing smectite clay as a first ingredient of the composition, 10% (w/w) to about 35% (w/w) of a second ingredient of the composition consisting essentially of whole yeast, non-whole yeast yeast mannan, non-whole yeast yeast mannan oligosaccharide, non-whole yeast yeast beta glucan, non-whole yeast yeast cell component, non-whole yeast yeast cell wall or citric acid press cake, and about 5% (w/w) to about 10% (w/w) of a glutamate as a third ingredient of the composition, wherein the administering of the composition is from 100 to 1000 mg/kg body weight/day or the administering is through the composition being present in a feed in an amount comprising about 0.05% (w/w) to about 0.50% (w/w) of the feed, to thereby treat the bacterial enteric disease or mitigate the effects of exposure to the bacterial enteric disease causing organism comprising a *Clostridium*.

2. The method of claim 1 wherein the *Clostridium*-toxin adsorbing smectite clay comprises a dioctahedral smectite.

3. The method of claim 2 wherein a dioctahedral smectite comprises a montmorillonite clay.

4. The method of claim 3, wherein the montmorillonite clay comprises a calcium montmorillonite clay.

5. The method of claim 4, wherein the calcium montmorillonite clay comprises a heat-treated calcium montmorillonite clay.

6. The method of claim 5, wherein in the heat treatment of the calcium montmorillonite clay, the calcium montmorillonite clay is heated to between about 100° C. to about 800° C.

7. The method of any one of claims 1 to 6, wherein the clay has a particle size of about 20 to 50 microns.

8. The method of any one of claims 1-6, wherein the second ingredient consists essentially of citric acid press cake.

9. The method of claim 7, wherein the second ingredient consists essentially of citric acid press cake.

10. The method of any one of claims 1-6, wherein the second ingredient is obtained from a *Pichia gnilliermondii*.

11. The method of claim 7, wherein the second ingredient is obtained from a *Pichia gnilliermondii*.

12. The method of claim 8, wherein the second ingredient is obtained from a *Pichia gnilliermondii*.

13. The method of claim 9, wherein the second ingredient is obtained from a *Pichia gnilliermondii*.

14. The method of any one of claims 1-6, wherein the glutamate comprises monosodium glutamate; or the glutamate comprises a glutamic acid, α-ketoglutarate, glutamine, L-glutamic acid or L-glutamine.

15. The method of any one of claims 1-6, wherein the glutamate comprises monosodium glutamate.

16. The method of claim 7, wherein the glutamate comprises monosodium glutamate.

17. The method of claim 8, wherein the glutamate comprises monosodium glutamate.

18. The method of claim 9, wherein the glutamate comprises monosodium glutamate.

19. The method of claim 10, wherein the glutamate comprises monosodium glutamate.

20. The method of claim 11, wherein the glutamate comprises monosodium glutamate.

21. The method of claim 12, wherein the glutamate comprises monosodium glutamate.

22. The method of claim 13, wherein the glutamate comprises monosodium glutamate.

23. The method of any one of claims 1-6, wherein the composition is present in a feed in an amount comprising about 0.05% (w/w) to about 0.50% (w/w) of the feed.

24. The method of claim 22, wherein the composition is present in a feed in an amount comprising about 0.05% (w/w) to about 0.50% (w/w) of the feed.

25. The method of claim 24 wherein the composition is present in a feed in an amount comprising about 0.05% (w/w) to about 0.35% (w/w) of the feed.

26. The method of claim 24 wherein the composition is present in a feed in an amount comprising about 0.25% (w/w) of the feed.

27. The method of any one of claims 1-6, wherein the composition comprises about 60% (w/w) of the first ingredient and about 35% (w/w) of the second ingredient and about 5% of the third ingredient, or about 80% of the first ingredient and about 10% (w/w) of the second ingredient and about 10% of the third ingredient.

28. The method of any one of claims 1-6, wherein the avian is a chicken, duck, goose, turkey, quail, or squab.

29. The method of claim 22, wherein the avian is a chicken, duck, goose, turkey, quail, or squab.

30. The method of claim 25, wherein the avian is a chicken, duck, goose, turkey, quail, or squab.

31. The method of claim 26, wherein the avian is a chicken, duck, goose, turkey, quail, or squab.

32. The method of any one of claims claim 28, wherein the method is for treating the enteric disease comprising bacterial enteric disease comprising Necrotic Enteritis (NE) in an avian or pig in need thereof.

33. The method of claim 29, wherein the method is for treating the enteric disease comprising bacterial enteric disease comprising Necrotic Enteritis (NE) in an avian or pig in need thereof.

34. The method of claim 30, wherein the method is for treating the enteric disease comprising bacterial enteric disease comprising Necrotic Enteritis (NE) in an avian or pig in need thereof.

35. The method of claim 31, wherein the method is for treating the enteric disease comprising bacterial enteric disease comprising Necrotic Enteritis (NE) in an avian or pig in need thereof.

36. The method of any one of claims claim 28, wherein the method is for mitigating the effects of exposure to bacterial enteric disease causing organism comprising *Clostridium*.

37. The method of claim 29, wherein the method is for mitigating the effects of exposure to bacterial enteric disease causing organism comprising *Clostridium*.

38. The method of claim 30, wherein the method is for mitigating the effects of exposure to bacterial enteric disease causing organism comprising *Clostridium*.

39. The method of claim 31, wherein the method is for mitigating the effects of exposure to bacterial enteric disease causing organism comprising *Clostridium*.

40. A feed comprising a composition for treating an enteric disease comprising a bacterial enteric disease comprising Necrotic Enteritis (NE) or mitigating the effects of exposure to a bacterial enteric disease causing organism comprising a *Clostridium* in an avian or pig susceptible to the enteric disease comprising a mixture of 50 to 80% (w/w) of a *Clostridium*-toxin adsorbing smectite clay as a first ingredient of the composition, 10% (w/w) to about 35% (w/w) of a second ingredient of the composition consisting essentially of whole yeast, non-whole yeast yeast mannan, non-whole yeast yeast mannan oligosaccharide, non-whole yeast yeast beta glucan, non-whole yeast yeast cell component, non-whole yeast yeast cell wall or citric acid press cake, and about 5% (w/w) to about 10% (w/w) of a glutamate as a third ingredient of the composition, wherein the composition is present in the feed in an amount comprising about 0.05% (w/w) to about 0.50% (w/w) of the feed.

41. The feed of claim 40, wherein the *Clostridium*-toxin adsorbing smectite clay comprises a dioctahedral smectite.

42. The feed of claim 41 wherein a dioctahedral smectite comprises a montmorillonite clay.

43. The feed of claim 42, wherein the montmorillonite clay comprises a calcium montmorillonite clay.

44. The feed of claim 43, wherein the calcium montmorillonite clay comprises a heat-treated calcium montmorillonite clay.

45. The feed of claim 44, wherein in the heat treatment of the calcium montmorillonite clay, the calcium montmorillonite clay is heated to between about 100° C. to about 800° C.

46. The feed of any one of claims 40 to 45, wherein the clay has a particle size of about 20 to 50 microns.

47. The feed of any one of claims 40-45, wherein the second ingredient consists essentially of citric acid press cake.

48. The feed of claim 46, wherein the second ingredient consists essentially of citric acid press cake.

49. The feed of any one of claims 40-45, wherein the second ingredient is obtained from a *Pichia gnilliermondii.*

50. The feed of claim 46, wherein the second ingredient is obtained from a *Pichia gnilliermondii.*

51. The feed of claim 47, wherein the second ingredient is obtained from a *Pichia gnilliermondii.*

52. The feed of claim 48, wherein the second ingredient is obtained from a *Pichia gnilliermondii.*

53. The feed of any one of claims 40-45, wherein the glutamate comprises monosodium glutamate; or the glutamate comprises a glutamic acid, α-ketoglutarate, glutamine, L-glutamic acid or L-glutamine.

54. The feed of any one of claims 40-45, wherein the glutamate comprises monosodium glutamate.

55. The feed of claim 46, wherein the glutamate comprises monosodium glutamate.

56. The feed of claim 47, wherein the glutamate comprises monosodium glutamate.

57. The feed of claim 48, wherein the glutamate comprises monosodium glutamate.

58. The feed of claim 49, wherein the glutamate comprises monosodium glutamate.

59. The feed of claim 50, wherein the glutamate comprises monosodium glutamate.

60. The feed of claim 51, wherein the glutamate comprises monosodium glutamate.

61. The feed of claim 52, wherein the glutamate comprises monosodium glutamate.

62. The feed of any one of claims 40-45, wherein the composition is present in the feed in an amount comprising about 0.05% (w/w) to about 0.35% (w/w) of the feed.

63. The feed of claim 53, wherein the composition is present in the feed in an amount comprising about 0.05% (w/w) to about 0.35% (w/w) of the feed.

64. The feed of claim 55 wherein the composition is present in a feed in an amount comprising about 0.05% (w/w) to about 0.35% (w/w) of the feed.

65. The feed of claim 55 wherein the composition is present in a feed in an amount comprising about 0.25% (w/w) of the feed.

66. The feed of any one of claims 40-45, wherein the composition comprises about 60% (w/w) of the first ingredient and about 35% (w/w) of the second ingredient and about 5% of the third ingredient, or about 80% of the first ingredient and about 10% (w/w) of the second ingredient and about 10% of the third ingredient.

* * * * *